(12) United States Patent
Horvers

(10) Patent No.: US 9,610,427 B2
(45) Date of Patent: Apr. 4, 2017

(54) NARROW PROFILE COMPOSITION-RELEASING EXPANDABLE MEDICAL BALLOON CATHETER

(71) Applicant: WELLINQ MEDICAL B.V., Leek (NL)

(72) Inventor: Ronald Adrianus Maria Horvers, Geldrop (NL)

(73) Assignee: WELLINQ MEDICAL B.V., Leek (NL)

( * ) Notice: Subject to any disclaimer, the term of this patent is extended or adjusted under 35 U.S.C. 154(b) by 0 days.

(21) Appl. No.: 15/085,745

(22) Filed: Mar. 30, 2016

(65) Prior Publication Data
US 2016/0213895 A1    Jul. 28, 2016

Related U.S. Application Data

(62) Division of application No. 13/510,400, filed as application No. PCT/EP2010/067838 on Nov. 19, 2010.
(Continued)

(30) Foreign Application Priority Data

Nov. 19, 2009 (EP) .................................. 09176447

(51) Int. Cl.
*A61M 25/10* (2013.01)
*A61F 2/958* (2013.01)
*A61L 29/16* (2006.01)

(52) U.S. Cl.
CPC ......... *A61M 25/1029* (2013.01); *A61F 2/958* (2013.01); *A61L 29/16* (2013.01); *A61M 25/10* (2013.01); *A61M 25/1002* (2013.01); *A61M 25/1027* (2013.01); *A61L 2300/406* (2013.01); *A61L 2300/416* (2013.01);
(Continued)

(58) Field of Classification Search
CPC .................. A61M 25/1029; A61M 2025/1031
See application file for complete search history.

(56) References Cited

U.S. PATENT DOCUMENTS

2006/0020243 A1* 1/2006 Speck ................... A61L 29/085
604/103.02
2010/0076539 A1* 3/2010 Klocke ................... A61F 2/958
623/1.11

OTHER PUBLICATIONS

Certified priority document retrieved from WIPO. EP 09176447. 2—filed Nov. 19, 2009 pp. 1-36.*

* cited by examiner

*Primary Examiner* — Aradhana Sasan
(74) *Attorney, Agent, or Firm* — Knobbe, Martens, Olson & Bear, LLP

(57) ABSTRACT

A process for making a folded composition-eluting balloon catheter includes coating one or both surfaces of a one or more foldable wings with a hydrophilic coating, applying a composition as a coating on the coated surface and providing the composition within a fold of the one or more foldable wings, and folding the one or more foldable wings to seal the composition by the one or more foldable wings to prevent/reduce its release until after inflation of the balloon. Another process for making a folded composition-eluting balloon catheter includes coating one or both surfaces of the one or more foldable wings with a hydrophilic coating-composition mixture and providing the composition by the one or more foldable wings, and folding the one or more foldable wings to seal the composition between the fold of the one or more foldable wings to prevent/reduce its release until after an inflation of the balloon.

22 Claims, 7 Drawing Sheets

Related U.S. Application Data

(60) Provisional application No. 61/262,712, filed on Nov. 19, 2009.

(52) U.S. Cl.
CPC ............... *A61M 2025/1004* (2013.01); *A61M 2025/105* (2013.01); *A61M 2025/1031* (2013.01)

NARROW PROFILE COMPOSITION-RELEASING EXPANDABLE MEDICAL BALLOON CATHETER

CROSS REFERENCE TO RELATED APPLICATIONS

This application is a divisional application of U.S. application Ser. No. 13/510,400, filed May 17, 2012, which was the U.S. National Phase Application under 35 U.S.C. §371 of International Application No. PCT/EP2010/067838, filed Nov. 19, 2010, and published as US 2012/0232640 A1 on Sep. 13, 2012 and as WO/2011/061295 A1 on May 26, 2011, which claimed the benefit of U.S. Application No. 61/262,712 filed Nov. 19, 2009 and European Application No. EP 09176447.2, filed Nov. 19, 2009. All of the foregoing applications, as well as any and all applications for which a foreign or a domestic priority is claimed as identified in the Application Data Sheet filed herewith are hereby incorporated by reference in their entirety.

FIELD

The present invention is in the field of drug-eluting medical balloon catheters. More specifically, it is in the field of medical balloon catheters having controllable composition release, particularly a limited release prior to balloon expansion at the site of treatment.

BACKGROUND

Balloon catheters of various forms are commonly employed in a number of surgical procedures. These devices comprise a thin catheter tube that can be guided through a body conduit of a patient such as a blood vessel and a distensible balloon located at the distal end of the catheter tube. Actuation of the balloon is accomplished through use of a fluid filled syringe or similar device that can inflate the balloon by filling it with fluid (e.g., water or saline solution or contrast solution) to a desired degree of expansion and then deflate the balloon by withdrawing the fluid back into the syringe.

In use, a physician will guide the balloon catheter into a desired position and then expand the balloon to accomplish the desired result (e.g., clear a blockage, or install or actuate some other device). Once the procedure is accomplished, the balloon is then deflated and withdrawn from the blood vessel.

The balloon is commonly used to deploy a stent in order to permanently open a blockage, which remains in place after the catheter is withdrawn. The stent may be coated with a substance that prevent tissue stenosis/restenosis or promotes healing of the injury caused by opening the vessel.

While the use of a stent is established for blocked vessels, it is not always the most appropriate treatment. Stent deployment is known to cause damage to the vessel wall which in itself can be the cause of further vessel closure. When the stent is of the drug eluting variety, it is not possible to stop treatment without stent removal, entailing additional surgical procedures. Delivering a precise and/or intermittent treatment is also precluded by a drug-eluting stent, thus treatment optimization is not possible. Moreover, a stent is not suitable as a vehicle of high-dose treatment regimens. In addition, it is not suitable for treating large cavities, or cavities having a non-cylindrical profile.

Coated balloons are useful for addressing the above, and are known in the art for the delivery of active pharmaceutical substances. US 2010/0076539, US 2009/0054837, WO 2009/111712, DE 20 2009 006 632, and US 2006/0020243 describe coated balloons in which the active pharmaceutical substance is held between the balloon folds. A problem in the art is systemic toxicity which arises from partial unfolding of the wings during advancement of the catheter through the vasculature, the bends of which can loosen the wings of conventionally folded balloons.

The present invention aims to overcome the problem of periodic delivery of medicaments to cylindrical or non-cylindrical bodily cavities and to provide a means to deliver doses that avoids systemic toxicity.

SUMMARY

One embodiment of the invention is a composition-eluting balloon catheter (100) having a proximal (20) and distal (15) end, comprising an elongated catheter tube (6) with an inflation lumen (7) extending therewithin and at least one inflatable balloon (4) towards the distal end (15) in fluid communication with the inflation lumen (7), wherein:
 the balloon (4) in the uninflated condition is configured as a one or a plurality of folded wings (10', 10"), and
 composition (12', 12") is provided essentially exclusively within the folds of the wings (10', 10") in such a manner that release of the composition is reduced or prevented until after inflation of the balloon has commenced.

Another embodiment of the invention is composition-eluting balloon catheter (100) having a proximal (20) and distal (15) end, comprising an elongated catheter tube (6) with an inflation lumen (7) extending therewithin and at least one inflatable balloon (4) having a central longitudinal balloon axis (B-B') towards the distal end (15) in fluid communication with the inflation lumen (7), wherein:
 the balloon (4) in the uninflated condition is configured as a one or a plurality of folded wings (10', 10"), and
 composition (12', 12") is provided essentially exclusively within the folds of the wings (10', 10") in such a manner that release of the composition is reduced or prevented until after inflation of the balloon has commenced,
 wherein the balloon (4) in the folded condition is further provided with a relief structure (30) comprising at least one groove on the outside of the folded wings (10', 10"), configured to substantially reduce in depth in an inflated state of the balloon (4), and
 whereby the at least one groove is essentially devoid of composition (12', 12").

A particular embodiment of the invention is a balloon catheter as described above, wherein the at least one groove (32) has a directional component which is transverse to the central longitudinal axis (B-B') of the balloon (4).

Another particular embodiment of the invention is a balloon catheter as described above, wherein the wings (10', 10") are folded around a central longitudinal balloon axis (B-B') of the balloon (4).

Another particular embodiment of the invention is a balloon catheter as described above, wherein the outside of the balloon (4) in the uninflated state is provided with a relief structure (30), configured to substantially reduce in depth in an inflated state of the balloon.

Another particular embodiment of the invention is a balloon catheter as described above, wherein in an uninflated state the relief structure comprises at least one groove (32), wherein the at least one groove (32) has a directional component which is transverse to a longitudinal axis of the balloon (4).

Another particular embodiment of the invention is a balloon catheter as described above, whereby the at least one groove (32) extends at a predetermined angle with regard to the longitudinal axis of the balloon (4).

Another particular embodiment of the invention is a balloon catheter as described above, wherein at least two grooves (33, 34) extend from the distal end (15) to the proximal end (20) of the balloon (4) and cross each other.

Another particular embodiment of the invention is a balloon catheter as described above, whereby the at least one groove (32) is ring or oval shaped, and has a directional component which is transverse to a central longitudinal axis (B-B') of the balloon (4).

Another particular embodiment of the invention is a balloon catheter as described above, wherein the at least one groove (32) crosses the outer edge of at least one folded wing (10', 10").

Another particular embodiment of the invention is a balloon catheter as described above, whereby the groove (32) extends from the distal end (15) to the proximal end (20) of the balloon (4), over the outside surface thereof.

Another particular embodiment of the invention is a balloon catheter as described above, wherein at least two grooves (33, 34) extend from the distal end (15) to the proximal end (20) of the balloon (4) and cross each other.

Another particular embodiment of the invention is a balloon catheter as described above, wherein the composition comprises paclitaxel.

Another particular embodiment of the invention is a balloon catheter as described above, wherein the composition comprises:
  one or more of paclitaxel, melatonin, thalidomide, sirolimus, zotarolimus, everolimus, biolimus, 17-β estradiol, actinomucin D, docetaxel, and/or any derivatives thereof, or
  one or more of cis-platin, paclitaxel, etoposide, amasecrine, teniposide, irinotecan, toptecan, doxorubicin, epirubicin, bleomycin, and/or any derivatives thereof, or
  one or more of penicillin, erythromycin, ampicillin, clindamycin, tetracycline, streptomycin, amoxicillin, cefaclor, lincomycin, clarithromycin, cephalosporins, azithromycin, doxycycline, ciprofloxacin, cefuroxime, levofloxacin, chloramphenicol, minocycline, penicillins, vancomycin, kanamycin, gentamicins, neomycin, ceftriaxone, bacitracin, oxacillin, cloxacillin, cephalothin, amoxicillin, dicloxacillin, aminoglycosides, methicillin, carbenicillin, gentamicin, trimethoprim, oxytetracycline, rifampin, tetracyclines, polymyxins, cephalexin, chlortetracycline, metronidazole and/or any derivatives thereof.

Another particular embodiment of the invention is a balloon catheter as described above, wherein the balloon is provided with a hydrophilic coating onto which the composition (12', 12") is at least partially disposed.

Another particular embodiment of the invention is a balloon catheter as described above, wherein the hydrophilic coating is any of polyvinylpyrrolidone (PVP) or copolymers containing N-vinylpyrrolidone, poly (meth) acrylic acid or copolymers containing (meth) acrylic acid or (meth) acrylic acid esters, polyacrylamides, polyvinylalcohol and copolymers of partially saponified vinylacetate copolymers, polyethylenglycol, polyvinylmethylether, polyvinylmethylether-maleic anhydride and copolymers containing maleic-anhydride or maleic-acidesters or copolymers containing vinylmethylether, or copolymers thereof, or water soluble polysaccharides or derivatives thereof such as carboxymethylcellulose (CMC) or hydroxyethylcellulose or Xanthane or a derivative thereof to the liquid for wetting a hydrophilic coating.

Another particular embodiment of the invention is a balloon catheter as described above, further provided with a stent.

Another particular embodiment of the invention is a balloon catheter as described above, wherein the stent is made from any of stainless steel, tantalum, titanium alloy, nitinol, cobalt alloy, cobalt-chromium-nickel alloy, cobalt-chromium alloy, cobalt-chromium F562, or magnesium alloys.

Another particular embodiment of the invention is a balloon catheter as described above, obtainable by a process comprising the steps:
  a) coating one or both surfaces of a balloon wing (10', 10") at least partially with a hydrophilic coating;
  b) applying the composition (12', 12") in a solution of organic solvent preferably methanol, propanol, acetone, or ethyl acetate, more preferably ethanol, at least partially over the coated surface;
  c) folding the balloon wings (10', 10") around the central longitudinal balloon axis (B-B') such that applied composition (12', 12") is disposed within the folds of the wings; and
  d) removing excess composition (12', 12") from the surface of the folded balloon.

Another particular embodiment of the invention is a balloon catheter as described above, further comprising the step of applying a relief structure as defined above, to the surface of the balloon after folding.

Another particular embodiment of the invention is a balloon catheter as described above, that is a rapid exchange catheter.

Another particular embodiment of the invention is a balloon catheter as described above, that is an over-the-wire catheter.

Another embodiment of the invention is a process for obtaining a composition-eluting balloon catheter (100) having a proximal (20) and distal (15) end, comprising an elongated catheter tube (6) with an inflation lumen (7) extending therewithin and at least one inflatable balloon (4) having a central longitudinal balloon axis (B-B') towards the distal end (15) in fluid communication with the inflation lumen (7), wherein the balloon (4) in the uninflated condition is configured as one or a plurality of folded wings (10', 10") comprising the steps:
  a) applying the composition (12', 12") at least partially over one or both surfaces of the balloon wing;
  b) folding the balloon wings (10', 10") around the central longitudinal balloon axis (B-B') such that applied composition (12', 12") is disposed within the folds of the wings;
  c) removing excess composition (12', 12") from the surface of the folded balloon; and
  d) applying a relief structure (30) to the balloon (4) in the folded condition, comprising at least one groove on the outside of the folded wings (10', 10"), configured to substantially reduce in depth in an inflated state of the balloon (4), which at least one groove is essentially devoid of composition (12', 12").

A particular embodiment of the invention is a process as described above, wherein:
  one or both surfaces of the balloon wings (10', 10") are at least partially with a hydrophilic coating, prior to application of the composition; and the composition (12', 12") is applied in a solution of organic solvent preferably methanol, propanol, acetone, or ethyl acetate, more preferably ethanol, at least partially over the coated surface;

Another particular embodiment of the invention is a process as described above, wherein the relief structure has one or more of the features described above.

Another embodiment of the invention is a composition-eluting balloon catheter (100) obtainable by a process described above.

Another particular embodiment of the invention is a composition-eluting balloon catheter (100), further provided with a guidewire lumen for a rapid exchange catheter or an over the wire catheter mode of operation.

DETAILED DESCRIPTION

Figure 1:
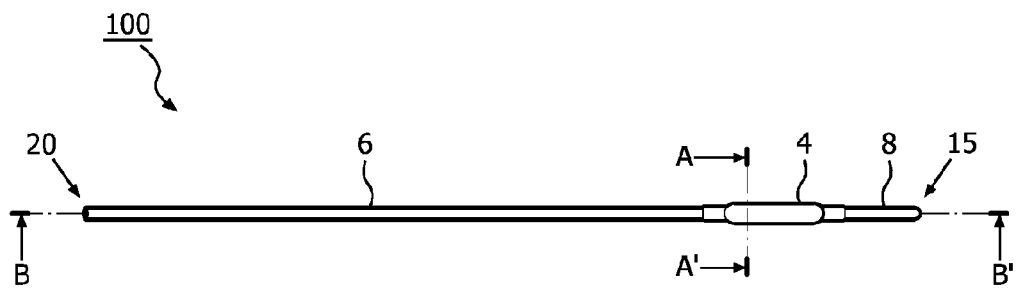
FIG. 1 shows a perspective view of a composition-eluting medical balloon catheter in the uninflated condition according to a particular embodiment of the invention.

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a medicament" means one medicament or more than one medicament.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of articles, and can also include 1.5, 2, 2.75 and 3.80, when referring to, for example, measurements).

The terms "distal", "distal end", "proximal" and "proximal end" are used through the specification, and are terms generally understood in the field to mean towards (proximal) or away (distal) from the surgeon side of the apparatus. Thus, "proximal (end)" means towards the surgeon side and, therefore, away from the patient side. Conversely, "distal (end)" means towards the patient side and, therefore, away from the surgeon side.

The present invention concerns a composition (drug or medicament)-eluting balloon catheter configured to release composition after inflation of the balloon has been initiated. The balloon is suitable for the delivery of composition to tissue and cells present in a cavity of a subject, when the balloon is inflated and the balloon contacts at least part of the cavity wall. The balloon in the uninflated condition comprises one or a plurality of folded wings, and composition is provided within the folds of the wings, in such a manner that release of the composition is reduced or prevented until after inflation of the balloon has been initiated. The composition is present essentially exclusively within the balloon folds. In other words, the outer surface of the folded balloon is essentially devoid of composition. The folds protect the composition from exposure to an environment, such as a liquid environment, that would otherwise initiate diffusion. In other words, the use of the folds reduces or prevents natural diffusion in situ of composition prior to inflation. In cases where the site of treatment is located some distance from the point of entry of the catheter, it can take a surgeon time to advance and position the balloon correctly e.g. when advanced along the vasculature from an entry point in the groin to a vessel in the vicinity of the heart. In cases where a very high dose of medicament is to be administered, the balloon is disposed with a high concentration of active ingredient which will commence diffusion from the moment it enters an aqueous environment for example in the vasculature. The arrangement of the present invention substantially limits unwarranted diffusion, reducing systemic toxicity and increasing locally-deliverable dose. Moreover, it provides a drug-eluting catheter having a substantially reduced profile.

The medical balloon catheter is of any design where a catheter is disposed with a balloon. Typically, it has a proximal end and distal end, and comprises an elongated catheter tube with an inflation lumen extending therewithin and at least one inflatable balloon towards the distal end in fluid communication with the catheter tube inflation lumen. The inflation lumen is open at the proximal end, that permits the catheter tube to couple with an inflation means such as a syringe. The medical balloon catheter may be extended at the distal end by a flexible tip. The catheter may be a rapid-exchange or over-the-wire type which types are well understood in the art.

The size of the medical balloon catheter is sufficiently narrow to introduce through the appropriate passage way e.g. nasopharyngeal route, vaginal and cervical route, or through a skin puncture.

Figure 1A:
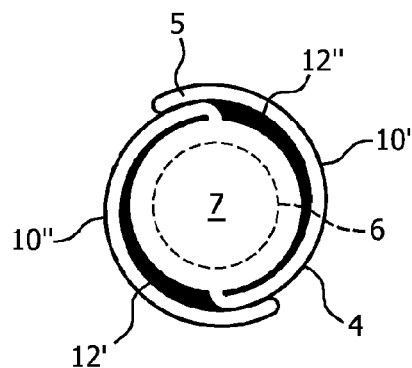
FIG. 1A shows a cross-sectional view through a composition-eluting balloon of the catheter according to a particular embodiment of the invention. The view is a cross-section through the line A-A' in FIG. 1 and perpendicular to the plane of the page.

FIG. 1 shows a typical balloon catheter in the uninflated state provided with folded wings, and FIG. 1A shows a transverse cross-section (A-A') through the balloon of FIG. 1. With reference to FIGS. 1 and 1A, a balloon catheter 100 of the invention comprises a balloon 4 mounted at the distal end 15 of an elongated flexible shaft 6 and terminating in a flexible tip 8. Balloon 4 has a balloon wall. The catheter 100 may be conventional in construction, providing an inflation lumen 7 in fluid communication with a balloon 4 lumen 5 for inflation and deflation.

The lumen is open at the proximal end. The catheter 100 allows inflation of the balloon 4 after placement in the cavity. Once in the cavity and after inflation, the catheter 100 remains in place for the duration of the treatment. It may provide treatments in addition to those delivered by the balloon 4, for example, through the catheter shaft 6. For instance, the catheter 100 may also be used to deliver circulating heating fluid, circulating cooling fluid, liquid medicament, radiopaque liquid tracer or ionizing or non-ionizing radiation to the balloon whose radiation can pass through the wall of the balloon 4. The catheter 100 can be single or multichannel, depending on the requirements of inflation, guidewire lumens, and delivery of other substances. The catheter may be provided with a guidewire lumen. The catheter 100 may be suitable for advancement over a guidewire in an over-the-wire mode in which case a guidewire lumen is provided from distal to proximal end of total catheter, or rapid-exchange mode, in which case a distal side guidewire lumen and terminal ports are provided. The guidewire lumen may be disposed within the inflation lumen 7 of the shaft 6.

Figure 2:
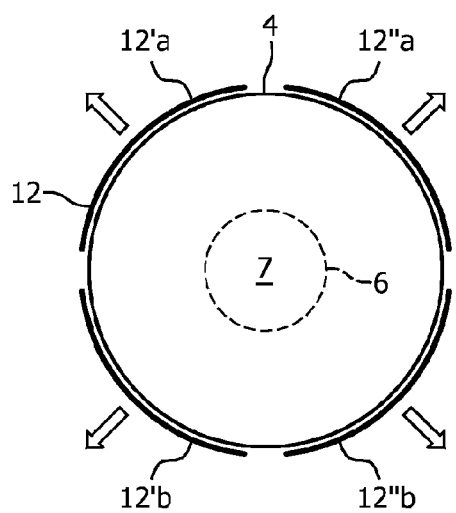
FIG. 2 shows the view of balloon of FIG. 1A in an inflated condition, and the disposition of coated composition. The view is a cross-sections through the line A-A' in FIG. 1 and perpendicular to the plane of the page.

The balloon in the uninflated condition comprises one or a plurality (e.g. 2, 3, 4, 5, 6) of folded wings 10', 10". The wings 10', 10" may be folded in any fashion, preferably folded around a central longitudinal balloon axis (B-B') as is well known in the art, and shown, for instance in FIG. 1A, to form the narrow cylindrical balloon profile. As is well understood, the wing 10', 10" structure is formed from the balloon in a flattened condition, each wing extending from the outer radial balloon edge towards the central (B-B') axis. Prior to folding, the wings may be radially extending, spaced from one another in the circumferential direction around the central longitudinal axis of the balloon. A wing 10', 10" in the folded condition is generally devoid of inflation medium, gaseous or fluid; FIGS. 1A, 3A to 3D indicate the presence of a void in the wings solely for reasons of clarity. The fold of a wing may be considered the region between an outside surface of a wing, and the surfaces it overlaps after folding. With reference to FIG. 1A, composition 12', 12" is provided at least partly between the fold of a wing 10', 10", the wing 10', 10" acting as a moisture-resistant barrier against exposure of the medicament to a fluidic environment in situ. Inflation causes the wings to unfold so exposing the composition 12', 12" to a fluidic environment and initiating diffusion. In the fully inflated condition, as shown in FIG. 2, the wings 10', 10" lose their form, adopting a tubular balloon 4 configuration. Depending on the degree of overlap between the folded wings, and the number of folds containing composition, almost the entire surface of the balloon 4 may be coated with said composition 12'*a*, 12'*b*, 12"*a*, 12"*b* in the inflated state. By taking advantage of the wing's inherent moisture impermeable property, no additional sheaths or covers are required to protect the composition during balloon placement. Thereby, the composition eluting balloon catheter has a narrow profile, and because no additional components are needed, the construction or adaptation costs are low.

The balloon is suitable for insertion into a cavity, which after insertion and inflation at least partly contacts the cavity wall of a subject for the delivery of composition. Various types of balloon are known with a plurality of shapes and features suited, after inflation, to the cavity shape and treatment regime. For example, a balloon after inflation may be longitudinal, ovoid, conical, cylindrical, barrel, hourglass, bullet shaped or any shape that can accommodate the cavity receiving treatment.

Figure 3A:
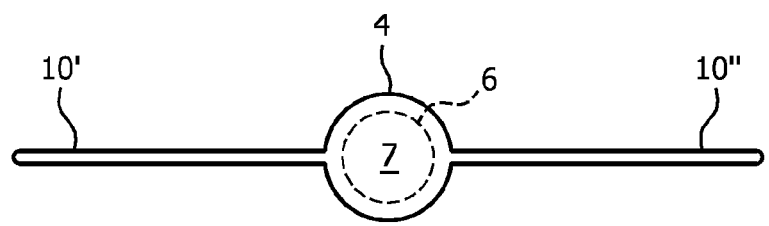
FIGS. 3A to 3D show the steps of folding composition-coated wings of a balloon in accordance with a particular embodiment of the invention; the views are cross-sections through the line A-A' in FIG. 1 and perpendicular to the plane of the page.
Figure 3B:
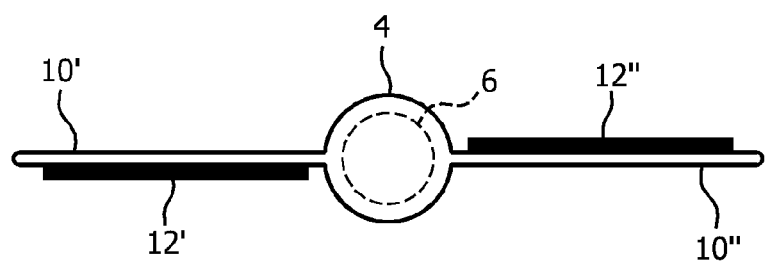
Figure 3C:
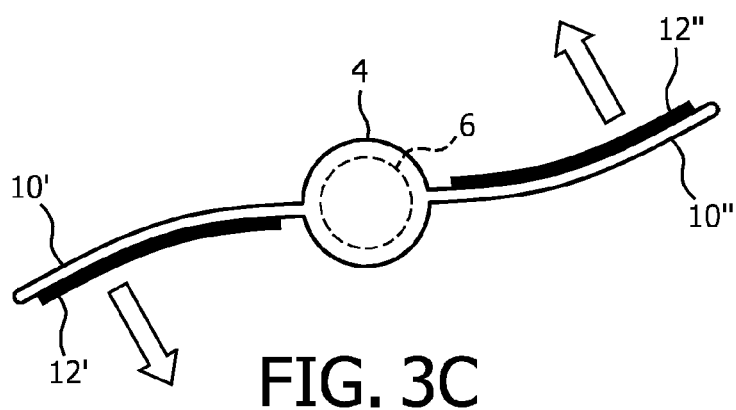
Figure 3D:
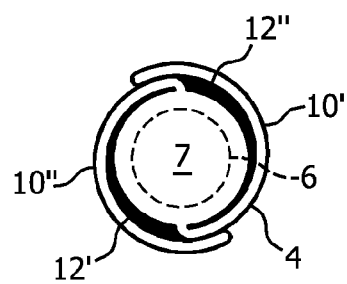

In preparing the balloon 4 according to the invention, the uninflated balloon is arranged, depending on the size of the balloon, into 1, 2, 3, 4, 5, or 6 wings 10', 10", in a manner known per se to provide a propeller-type profile as shown, for instance, in FIG. 3A, each wing having two opposing surfaces. In a preferred embodiment, one or both surfaces of a wing, (e.g. 1, 2, 3, 4, 5, 6 or more wings, preferably each and every wing) is at least partially coated with composition; in FIG. 3B one surface of each wing is partially coated with composition 12', 12". When one surface is coated, the composition coated surface is preferably that which folds towards the central longitudinal balloon axis (B-B'). Coating may be effected by dripping, dipping, brushing, or spraying the composition, or by any other means. The wings are folded (FIG. 3C) in a clock-wise or anti-clockwise direction, depending on the coated surface, such that the composition 12', 12" lies substantially in the fold created by the wing; in the case of FIG. 3C, the wings are folded in an anti-clockwise direction when viewed in the direction from the distal 15 to the proximal 20 end of the balloon 4. Folding creates a balloon (FIG. 3D) containing composition 12', 12" essentially sealed from the environment by virtue of the moisture impermeable balloon wings 10', 10". Excess composition on the folded balloon surface can be removed. The folded balloon so formed has compact and narrow profile that makes it possible to guide the balloon catheter through vessel and lumina. While the above provides a general guidance, the skilled person will understand the routine variations and adaptations that can be readily implemented; these variations also fall under the scope of the invention. For instance, FIG. 3B to 3C show medicament coated on one surface of each wing, however, the composition may also be at least partially coated on both surfaces, the excess composition removed, and/or the coating restricted to parts of the wing anticipated to form a fold.

The outer surface of the balloon 4 may be pre-treated with a hydrophilic substance i.e. prior to application of the composition. The hydrophilic substance acts as a base onto which the composition is applied. The balloon is first coated with the hydrophilic substance, then the hydrophilic substance is coated with the composition. The hydrophilic substance increases adhesion of the composition to the balloon 4 surface. One or both surfaces of each wing may be at least partially coated with hydrophilic substance. It is understood that when one surface of the wing is treated with hydrophilic substance, the same surface is provided with composition. When both surfaces of the wings are treated, the hydrophilic substance serves to increase the lubricity of the catheter during advancement to the site of treatment. Hydrophilic treatment may be effected by dripping, dipping, brushing, spraying the hydrophilic substance onto the balloon, or any other means. Once it has dried partially or completely, the composition may be later applied thereover. The balloon provided with the hydrophilic coating may apply to a balloon of the invention. It may also apply to any drug eluting balloon of the art or future balloon; the composition need not be restricted to the folds of the balloon, and the balloon may not necessarily be provided with the additional relief structure described below.

Hydrophilic substances are well known in the art, as coatings for medical devices. Whereas such coating is not particularly smooth when dry, so that the handling of the device may become inconvenient, it becomes extremely slippery when it is swelled with water, preferably immediately before introduction into the human body and thus ensures a substantially smooth introduction with a minimum of tissue damage.

Hydrophilic coatings are described variously in U.S. Pat. No. 3,967,728, WO 86/06284, GB 2 284 764, and U.S. Pat. No. 3,648,704 which are incorporated herein by reference.

Methods are known in the art for coating the surface of a balloon with a hydrophilic coating. These methods are most often based on the fact that the balloon to be provided with a hydrophilic surface coating, in the course of one or more process stages with intermediary drying and curing, is coated with one or more (mostly two) layers, which are brought to react with one another in various ways, for example, by polymerisation initiated by irradiation, by UV light, by graft polymerisation, by the formation of interpolymeric network structures, or by direct chemical reaction. Known hydrophilic coatings and processes for the application thereof are disclosed, for example, in DE 159,018, EP 0 389 632, EP 0 379 156, EP 0 454 293, EP 0 093 093 B2, GB 1,600,963, U.S. Pat. No. 4,119,094, U.S. Pat. No. 4,373,009, U.S. Pat. No. 4,792,914, U.S. Pat. No. 5,041,100 and U.S. Pat. No. 5,120,816, WO 90/05162 and WO 91/19756 which are incorporated herein by reference.

According to particular embodiments of the invention, the hydrophilic substance is coated onto the balloon by applying, in two stages or in one combined stage, on the balloon, a primer reactive with or adhesive to the balloon and then the actual hydrophilic substance.

The hydrophilic substance may comprise a hydrophilic polymer, for example, polyvinylpyrrolidone (PVP) or copolymers containing N-vinylpyrrolidone, poly (meth) acrylic acid or copolymers containing (meth) acrylic acid or (meth) acrylic acid esters, polyacrylamides, polyvinylalcohol and copolymers of partially saponified vinylacetate copolymers, polyethylenglycol, polyvinylmethylether, polyvinylmethylether-maleic anhydride and copolymers containing maleic-anhydride or maleic-acidesters or copolymers containing vinylmethylether, or copolymers thereof, or water soluble polysaccharides or derivatives thereof such as carboxymethylcellulose (CMC) or hydroxyethylcellulose or Xanthane or a derivative thereof to the liquid for wetting a hydrophilic coating. Suitable hydrophilic polymers may be mixtures of the preferred species stated above. In an especially preferred embodiment of the invention the hydrophilic substance comprises a polyvinyl pyrrolidone (PVP).

When the hydrophilic substance is polyvinyl pyrrolidone, the amount to be used according to the invention may vary and depends inter alia on the molecular weight of the specific PVP. The higher the molecular weight, the higher is the tendency of gelling. Thus, the use of higher amounts of low molecular weight PVP gives an effect similar to the use of lower amounts of a higher molecular weight PVP. The amount of a PVP of a given molecular weight PVP to be used is easily determined by the skilled in the art by routine experiments testing the water retention.

The composition may be applied to the balloon using any suitable technique such as dripping, dipping, brushing, spraying, or any other means. In a preferable embodiment the composition is applied in a solution of an organic solvent, such as methanol, ethanol, propanol, acetone, or ethyl acetate in high purity. The solvent evaporates after coating leaving little or no residue. Preferably, the organic solvent is selected to be fast-evaporating, leaving no or little residue.

The use of a hydrophilic coating and application of the composition in a solution of an organic solvent provides a uniform dispersion of medicament on the balloon, avoiding the formation of crystalline patches. Moreover, it provides a smooth surface. The combination also reduces or prevents the release of fragmented particles of composition upon expansion of the balloon, thereby delivering medicament locally to the wall of the cavity being treated, and reducing systemic release.

The present inventors have found that the composition, namely the medicament, is retained on the balloon pre-treated with a hydrophilic coating. After exposure of the uninflated balloon to an aqueous environment such as a water bath, the medicament is substantially retained. Retention of the medicament is observed even when the composition is not sealed within the balloon folds.

Additionally, the balloon pre-treated with hydrophilic substance advantageously substantially releases composition to the cavity wall only after inflation of the balloon. Release may be controlled by inflation and deflation, namely when the balloon is inflated, composition is released, and when the balloon is deflated, release of composition is effectively stopped. Where the balloon inflates and there is no contact by the balloon with the cavity wall, release of composition is minimised. This allows multiple inflation and deflation of the balloon in the same or at different locations, each inflation administering a separate dose.

In a particularly preferred embodiment, the composition comprises paclitaxel, or melatonin or a combination of both in ethanol that is applied to the balloon pre-treated with a hydrophilic coating. Using such a formulation, the solvent is rapidly evaporated leaving paclitaxel and/or melatonin evenly distributed, and without the formation of large crystals. Moreover, a good adhesion of the active compounds is achieved, the composition layer more resistant to the release of particulate medicament during or after balloon inflation.

Accordingly, in a particular embodiment of the invention is a process for obtaining a balloon catheter as described herein comprising the steps performed in the following order:

a) coating one or both surfaces of a balloon wing 10', 10" at least partially with a hydrophilic coating;

b) applying the composition 12', 12" in a solution of organic solvent preferably methanol, propanol, acetone, or ethyl acetate, more preferably ethanol, at least partially over the coated surface;

c) folding the balloon wings 10', 10" around the central longitudinal balloon axis (B-B') such that applied composition 12', 12" is disposed within the folds of the wings; and d) removing excess composition 12', 12" from the surface of the folded balloon.

A further embodiment of the invention is a balloon 4 as described herein obtainable by a process comprising the steps:

a) coating one or both surfaces of a balloon wing 10', 10" at least partially with a hydrophilic coating;

b) applying the composition 12, 12', 12" in a solution of organic solvent preferably methanol, propanol, acetone, or ethyl acetate, more preferably ethanol at least partially over the coated surfaces;

c) folding the balloon wings 10', 10" around the central longitudinal balloon axis B-B' such that applied composition 12', 12" is disposed within the folds of the wings; and d) removing excess composition 12', 12" from the surface of the folded balloon.

As mentioned above, the hydrophilic coating may be applied to any balloon of the art or future balloon, and is not limited to the balloons described herein having composition exclusively between the folds and/or being provided with a relief structure (described below). Accordingly, one embodiment of the invention is a composition-eluting balloon catheter 100 having a proximal 20 and distal 15 end, comprising an elongated catheter tube 6 with an inflation lumen 7 extending therewithin and at least one inflatable balloon 4—having a central longitudinal balloon axis B-B'—towards the distal end 15 in fluid communication with the inflation lumen 7, wherein the composition 12', 12" is at least partially disposed over a hydrophilic coating provided on the balloon. Such balloon may optionally be provided with a stent, as discussed elsewhere herein.

Another embodiment of the invention is a process for obtaining a balloon as defined above comprising the steps performed in the following order:

a) coating one or both surfaces of a balloon wing (10', 10") at least partially with a hydrophilic coating;

b) applying the composition (12', 12") in a solution of organic solvent preferably methanol, propanol, acetone, or ethyl acetate, more preferably ethanol, at least partially over the coated surface;

c) folding the balloon wings (10', 10") around the central longitudinal balloon axis (B-B'), thereby obtaining a composition-eluting balloon.

Suitable hydrophilic coatings and examples of compositions are described elsewhere herein. Aspects and embodiments described herein in regard of the composition provided exclusively between the folds and/or being provided with a relief structure also apply to such balloons of the art or future balloons coated with the hydrophilic coating.

While the hydrophilic coating and composition and are described above as being separately and sequentially applied to the balloon, it will be appreciated that the composition may be applied to the outer surface of the balloon 4 as a mixture with a hydrophilic substance i.e. composition and hydrophilic substance are simultaneously applied.

Accordingly, in a particular embodiment of the invention is a process for obtaining a balloon catheter as described herein comprising the steps performed in the following order:

a) coating one or both surfaces of a balloon wing 10', 10" at least partially with a mixture comprising a hydrophilic coating and composition 12', 12", optionally in a solution of organic solvent preferably methanol, propanol, acetone, or ethyl acetate, more preferably ethanol;

c) folding the balloon wings 10', 10" around the central longitudinal balloon axis (B-B') such that applied mixture is disposed within the folds of the wings; and d) optionally removing excess mixture from the surface of the folded balloon.

Another embodiment of the invention is a process for obtaining a balloon as described above comprising the steps performed in the following order:

a) coating one or both surfaces of a balloon wing 10', 10" at least partially with a mixture comprising a hydrophilic coating and composition 12', 12", optionally in a solution of organic solvent preferably methanol, propanol, acetone, or ethyl acetate, more preferably ethanol;

b) folding the balloon wings 10', 10" around the central longitudinal balloon axis (B-B'), thereby obtaining a composition-eluting balloon.

The invention also provides a balloon catheter obtained by one of these processes. Suitable hydrophilic coatings and examples of compositions are described elsewhere herein. Aspects and embodiments described herein in regard of the composition provided exclusively between the folds and/or being provided with a relief structure also apply to such balloons of the art or future balloons coated with the hydrophilic coating.

The wings 10', 10" of the balloon 4 may be maintained in the folded condition by dint of a substance having light adhesive property present in the composition, or disposed over the wing edges. Alternatively or in addition, the folded wings may be subjected to a heat and/or pressure treatment to maintain their structure, the parameters of which will depend on the lability of the composition. Additionally or alternatively, and preferably, the folded state may be maintained by introducing a relief structure, namely a pattern of grooves applied to the outer surface of the folded wings of the balloon. When applied to a composition-eluting balloon, this relief structure technology is known as "Wing-Seal" herein. Accordingly, the processes for obtaining a balloon stent according to the present invention may further comprise the step of introducing a relief structure to the outer surface of the folded wings of the balloon as will be described below.

Figure 4A:
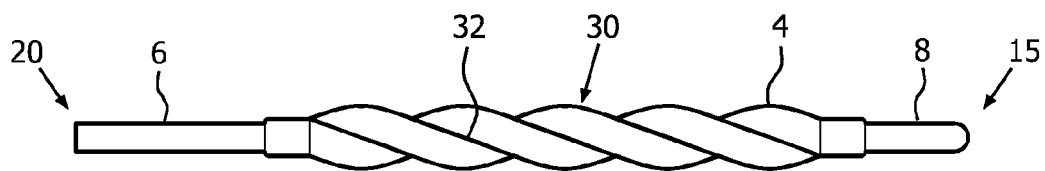
FIG. 4A shows a perspective view of a composition-eluting medical balloon portion of the catheter in the uninflated condition disposed with a relief pattern in the form of a single helical groove according to a particular embodiment of the invention.
Figure 4B:
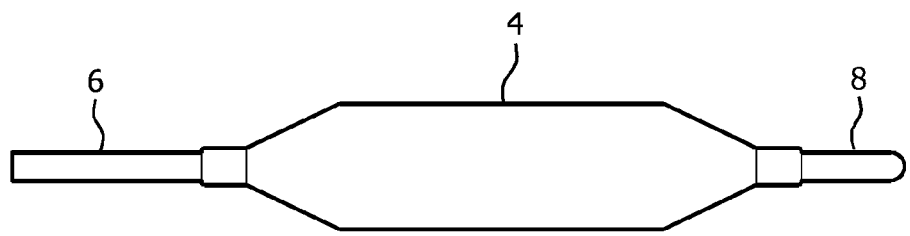
FIG. 4B shows a perspective view of a composition-eluting medical balloon of FIG. 4A in the inflated condition.
Figure 5A:
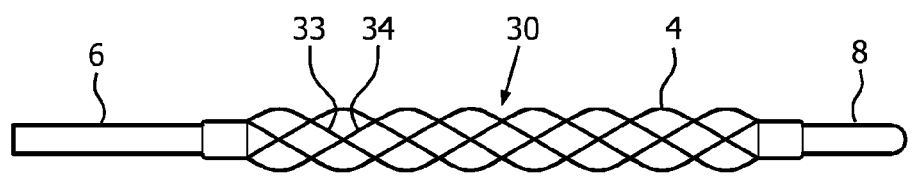
FIG. 5A shows a perspective view of a composition-eluting medical balloon portion of the catheter in the uninflated condition disposed with a relief pattern in the form of a two helical grooves according to a particular embodiment of the invention.
Figure 5B:
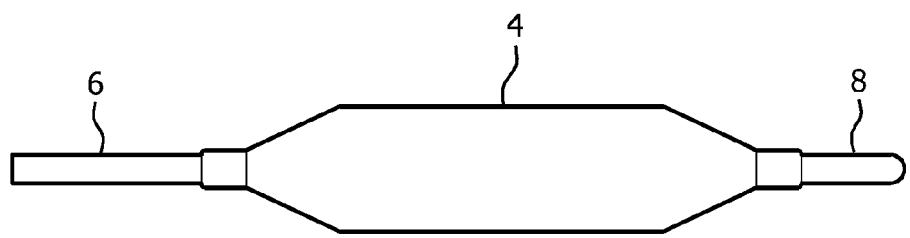
FIG. 5B shows a perspective view of a composition-eluting medical balloon catheter of FIG. 5A in the inflated condition.

According to particular embodiments of the invention, in an uninflated (folded) state (FIGS. 4A and 5A), the outside surface of balloon 4 has a relief structure 30 configured, in the inflated state, to reduce in depth (FIGS. 4B and 5B). In other words, the balloon 4 in the uninflated (folded) condition is further provided with a relief structure 30 comprising at least one groove on the outside of the plurality of folded wings 10', 10". Thus, in the uninflated condition, the relief has a certain (average) impression depth that, upon inflation, is substantially reduced i.e. it becomes more shallow; the relief structure may be flattened-out upon inflation. The relief structure not only gives the catheter its required flexibility, it also maintains the wings in a folded condition, and reduces fluid ingress into the wing folds. In particular, it prevents the balloon wings from partially unfolding during advancement of the catheter through the vasculature, the bends of which can loosen the wings of conventionally folded balloons. By employing a relief structure, the composition is effectively sealed between the wing folds, reducing composition diffusion even when the catheter is advanced through highly tortuous routes which normally flex the folded balloon and instigate unfolding. Since no additional membranes or bands placed over the balloon are needed to maintain balloon integrity, the balloon profile is also narrower.

According to particular embodiments, the balloon 4 in the uninflated condition is thus further provided with a relief structure 30 comprising at least one groove on the outside of the plurality of folded wings 10', 10". The at least one groove may be essentially devoid of composition. Where there is more than one groove, preferably each and every groove may be essentially devoid of composition.

In a particular embodiment according to FIGS. 4A and 4B, the relief structure 30 comprises at least one groove or indentation 32, which extends helically from the distal 15 to the proximal 20 end of the balloon 4, over the outside surface thereof. The uninflated balloon 4 has thereby obtained a helical relief surface. In the second embodiment according to FIGS. 5A and 5B, the relief structure 30 comprises two grooves 33, 34, which extend helically from the distal 15 to the proximal 20 end of the balloon 4 and thereby cross each other. The uninflated balloon 4 has hereby obtained a padded relief surface.

Other relief structures are possible, provided that the relief structure on the catheter creates the necessary sealing effect and flexibility in a direction transverse to the longitudinal direction of the balloon. For example, the relief structure may comprise a series of circumferential groves that are ring (O-shaped), oval or C-shaped. Generally, the groove has a directional component that is transverse to the longitudinal axis (B-B') of the balloon. The number of grooves may be 20, 30, 40, 50, 60, 70, 80, 90, 100, 110, 120, 130, 140 or more, or a value in the range between any two of the aforementioned value, depending on the size of the balloon.

One way of obtaining the relief structure as shown in the drawings is by winding a wire helically around the balloon 4 as described for instance in US 2003/0014100 and US 2003/0014070. If the wire is wound only in the forward direction, the structure according to FIG. 4A is obtained, and if the wire is also wound in the return direction, the structure in FIG. 5A is obtained. After the wire has been wound around the balloon pressure is raised inside of the balloon, in such a way that, in an uninflated state, the balloon obtains a relief structure that on dilating of the balloon at the dilatation site in the vessel or lumen will reduce in depth, for example, virtually or completely disappear. The balloon may optionally be heated while under the raised pressure. The precise temperate and duration of heating can be determined optimally according to the lability of the composition.

Instead of winding a wire, the balloon may be placed in a mould, which is provided with the relief pattern required in order for it to obtain, under raised pressure and optionally raised temperature, the relief structure required.

Another way to achieve the relief structure is to crimp the pattern onto the surface, i.e. by the application of radial pressure to the outer surface of the folded balloon. The radial pressure is applied by a press having a central press axis disposed with a plurality of press jaws, configured to move radially towards the central press axis. The pressing end of the press jaws are disposed with the relief structure, and impress on the folded balloon when the jaws are in the closed position. In such a way, a relief structure is imparted. In a preferred embodiment, the jaws may hammer the relief structure on to the balloon; according to one aspect of the invention, the jaws deliver a plurality of hammer blows. The hammer blows may be delivered at a frequency in the range of 1 to 200, 300, 400, 500, 600, 700, 800, 900, 1000 or more blows per second. Crimping devices suitable for applying the relief structure are well known in the art, for example, those manufactured by Fortimedix and Machine Solution Inc.

Before the balloon is provided with its relief structure, preferably it is folded in the usual way in order to reduce its profile. By applying the relief structure, the profile will be reduced still further as an additional, advantageous effect.

Note that, although it is not shown in the drawings, it is possible to provide the outside surface of the balloon with various helical grooves that cross each other.

A catheter 100 is made of any biocompatible materials known in the art of catheter construction. Suitable biocompatible materials include, but are not limited to polypropylene, polyethylene, polyurethanes, polyamide, poly(ethylene terephthalate) (PET) or polyesters and copolymers thereof for the shaft 6; and any suitable elastomeric polymer material having moisture impermeable properties, able to withstand inflation pressure, such as polyamide (e.g. PA11, PA12), nylons, PEBAX™, polyethylene, latex rubber, elastic, or plastic for the balloon 4. A typical balloon catheter useful for the present invention is described, for instance, in U.S. Pat. No. 5,490,839, however, the present invention is no way limited to the given instance, and can be applied to any medical balloon catheter.

The balloon 4 may optionally be provided with a stent. The stent is fitted at least partially, preferably entirely over the balloon 4. The stent is preferably a non-drug eluting stent, though drug-eluting stents are not excluded. As mentioned elsewhere herein, the balloon 4 disposed with the stent may or may not be provided with the aforementioned hydrophilic coating. Additionally or independently, said balloon may or may not have composition exclusively between the folds. Additionally or independently, said balloon may or may not have the aforementioned relief structure.

Stents have been extensively described in the art. For example they may be cylinders which are perforated with passages that are slots, ovoid, circular, regular, irregular or the like shape. They may also be composed of helically wound or serpentine wire structures in which the spaces between the wires form the passages. Stents may also be flat perforated structures that are subsequently rolled to form tubular structures or cylindrical structures that are woven, wrapped, drilled, etched or cut to form passages. A stent may also be combined with a graft to form a composite medical device, often referred to as a stent graft.

Stents may be made of biocompatible materials including biostable and bioabsorbable materials. Suitable biocompatible metals include, but are not limited to, stainless steel, tantalum, titanium alloys (including nitinol), and cobalt alloys (including cobalt-chromium-nickel alloys, cobalt-chromium alloy and cobalt-chromium F562). Stents may be made of biocompatible and bioabsorbable materials such as magnesium based alloys. Bioabsorbable stents may inserted at the site of treatment, and left in place. The structure of the bioabsorbable stent is degraded with time.

Suitable non-metallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, epsilon-caprolactone, etc. and blends thereof), lactide capronolactone, poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), elastin polypeptide co-polymer, polyurethane, starch, polysiloxane and their copolymers.

A stent can be balloon expandable or self-expanding. The stent may also be made from different sorts of wires, for instance from polymeric biodegradable wires containing the active compound, interweaved with the metallic struts of the stent (balloon expendable or self-expandable stent). Self-expanding stents may be braided, from flexible metal, such as special alloys, from nitinol, from phynox. Self-expandable stents made from nitinol may be laser cut.

According to the present invention, the composition-eluting balloon of the invention may be placed on or adjacent to cells or tissue present in a bodily cavity that require treatment. The invention is particularly suited to the delivery of a high dose of medicament over a short time period. The period will depend on the location of treatment, for instance, delivery to the wall of a blood vessel, which will cause blockage after balloon inflation, may necessitate a shorter delivery period compared with delivery to the wall of the oesophasgus. As a general guidance, the delivery period may be equal to or less than 10 seconds (s), 20 s, 30 s, 40 s, 50 s, 1 minute, 5 minutes, 10 minutes, 20 minutes, 30 minutes, 40 minutes, 50 minutes or 1 hour, or a value in the range between any two of the aforementioned values, preferably between 30 seconds and 10 minutes for use in the vasculature.

A medical balloon catheter may be inserted into a cavity, for instance, a blood vessel of a subject and advanced therein until the balloon is in the vicinity of the treatment site that might be a stenosed region. After inflation, the expanded balloon contacts the cavity wall, delivering composition to the surrounding tissue and cells for a period. When the delivery period has expired, the balloon is deflated and withdrawn; alternatively it may be re-inflated for a further delivery for a defined period.

A cavity may be a natural bodily cavity such as a duct, vascular duct, a bronchial duct, a biliary duct, the oesophasgus, digestive tract, urethral duct, uretheral duct, uterus, stomach, arteries, veins, urethral duct, aeric tract, the urogenital tract, nasopharyngeal area, the pharynx, the small and large bowels, the rectum, the trachea, the uterine cavity, the uterine cervix, the vagina, the urethra, and the bladder or colon. The natural cavity can be any walled cavity of a subject suitable for placing the balloon therein. Such cavity may be narrowed by a medical condition such as stenosis, cancer, benign tumours, or invasion of a cancer originating from the wall or passing through the wall of a duct.

The composition according to the invention comprises a medicament for the treatment of tissues and cells present in the cavity. Examples of medicaments suitable for the treatment of stenosis or restenosis include one or more of paclitaxel, taxol, melatonin, thalidomide, sirolimus, zotarolimus, everolimus, biolimus, 17-β estradiol, actinomucin D, docetaxel, and/or any derivatives thereof. The composition may comprise paclitaxel, melatonin, or a combination of paclitaxel and melatonin. A preferred medicament is paclitaxel, even more preferred is paclitaxel not in combination with melatonin.

Examples of medicaments suitable for the treatment of tumours include one or more of cis-platin, paclitaxel, etoposide, amasecrine, teniposide, irinotecan, toptecan, doxorubicin, epirubicin, bleomycin, and/or any derivatives thereof.

Examples of medicaments suitable for the treatment of bacterial infections include one or more of penicillin, erythromycin, ampicillin, clindamycin, tetracycline, streptomycin, amoxicillin, cefaclor, lincomycin, clarithromycin, cephalosporins, azithromycin, doxycycline, ciprofloxacin, cefuroxime, levofloxacin, chloramphenicol, minocycline, penicillins, vancomycin, kanamycin, gentamicins, neomycin, ceftriaxone, bacitracin, oxacillin, cloxacillin, cephalothin, amoxicillin, dicloxacillin, aminoglycosides, methicillin, carbenicillin, gentamicin, trimethoprim, oxytetracycline, rifampin, tetracyclines, polymyxins, cephalexin, chlortetracycline, metronidazole and/or any derivatives thereof.

It is not excluded that the medicament is provided in combination with a polymer (e.g. a controlled release polymer), however, it is preferred that no polymer is present in the composition. It is also preferred that the composition is not over-coated with a polymeric layer, though this option should not be excluded from the invention.

Paclitaxel and melatonin and its derivatives, and options for separate or simultaneous administration are described in more detail below.

Paclitaxel refers to native paclitaxel, paclitaxel analogues and derivatives thereof, including, for example, a natural or synthetic functional analogue of paclitaxel which has paclitaxel biological activity, as well as a fragment of paclitaxel having paclitaxel biological activity. Paclitaxel includes the native compound having formula (I). A compound which is a paclitaxel analogue refers to a compound which interferes with cellular mitosis by affecting microtubule formation and/or action, thereby producing antimitotic and anti-cellular proliferation effects.

(I)

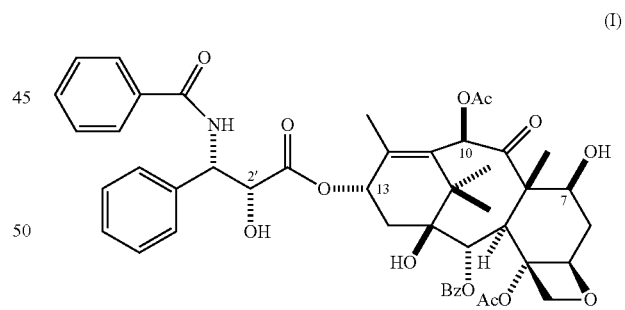

Methods of preparing paclitaxel and its analogues and derivatives are well-known in the art, and are described, for example, in U.S. Pat. Nos. 5,569,729; 5,565,478; 5,530,020; 5,527,924; 5,484,809; 5,475,120; 5,440,057; and 5,296,506. Paclitaxel and its analogues and derivatives are also available commercially. Synthetic paclitaxel, for example, can be obtained from Bristol-Myers Squibb Company, Oncology Division (Princeton, N.J.), under the registered trademark Taxol®.

An analogue of paclitaxel may have a structure according to formula II, whereby paclitaxel is modified at the C10 position. R may be any of Propionyl, Isobutyryl, Valeryl, Hexanoyl, Octanoyl, Decanoyl, Tridecanoyl, Methoxyacetyl, Methylthioacetyl, Methylsulfonylacetyl Acetoxyacetyl, Ethylformyl, Monosuccinyl, Crotonoyl, Acryloyl, Cyclopropanecarbonyl Cyclobutanecarbonyl, Cyclopentanecarbonyl, Cyclohexanecarbonyl, Hydrocinnamoyl, trans-Cinnamoyl, Phenylacetyl, Diphenylacetyl, Benzoyl 2-Chlorobenzoyl, 3-Chlorobenzoyl, 4-Chlorobenzoyl, 3,4-Dichlorobenzoyl, 3,5-Dichlorobenzoyl, 2,4-Dichlorobenzoyl, 3,5-Dibromobenzoyl, 4-Fluorobenzoyl, 3-Trifluoromethylbenzoyl, 4-Trifluoromethylbenzoyl, 3-Nitrobenzoyl, 4-Nitrobenzoyl, 3-Dimethylaminobenzoyl, 3-Methoxybenzoyl, 1-Naphthoyl, 2-Naphthoyl, 2-Quinolinecarbonyl, 3-Quinolinecarbonyl, 4-Quinolinecarbonyl, Indole-3-acetyl, Pyrrole-2-carbonyl, 1-Methyl-2-pyrrolecarbonyl, 2-Furoyl, 5-Bromofuroyl, 5-Nitrofuroyl, 3-Thiophenecarbonyl, 2-Thiophenecarbonyl, 2-Thiopheneacetyl, Picolinoyl, Isonicotinoyl, 5,6-Dichloronicotinoyl, 2-Methylnicotinoyl, 6-Methylnicotinoyl, 5-Bromonicotinoyl, 2-Pyrazinecarbonyl, Isobutyryl, Valeryl, Methoxyacetyl or Cyclohexanecarbonyl. Methods for the preparation of said analogues are described fully in Liu et al, Combinatorial chemistry and High Throughput Screening, 2002, Vol 5, p 39 to 48.

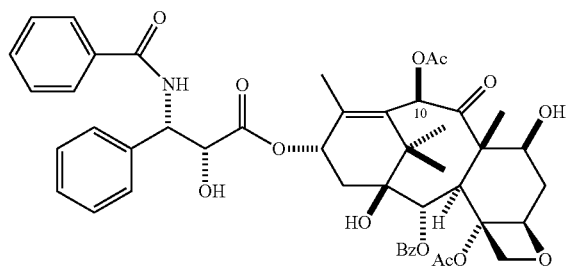

(II)

Taxol® and its analogues and derivatives have been used successfully to treat leukemias and tumors. In particular, Taxol® is useful in the treatment of breast, lung, and ovarian cancers. Moreover, paclitaxel may be synthesized in accordance with known organic chemistry procedures (Nerenberg et al., Total synthesis of the immunosuppressive agent (−)-discodermolide. *J. Amer. Chem. Soc.,* 115:12,621-12, 622, 1993) that are readily understood by one skilled in the art.

Melatonin (N-acetyl-5-methoxytryptamine) is a hormone secreted by the pineal gland. Melatonin is often prescribed for the treatment of sleep disturbances and jet-lag. The pharmacological activity of melatonin has been described in numerous publications. One of the early investigations of the pharmacological activity of melatonin was by Barchas and coworkers (Barchas et al. *Nature* 1967, 214, 919). Melatonin refers to native melatonin, melatonin analogues and derivatives thereof. An analogue of melatonin is a natural or synthetic functional variant of melatonin which has melatonin biological activity. An analogue of melatonin can be a compound which binds to the melatonin receptor; methods for identifying such melatonin analogues, for example by standard screening techniques, are well known in the art. An analogue may be a compound that binds to the melatonin receptor with an affinity better than $10^{-6}M$ in suitable buffer conditions.

Melatonin includes the native compound having formula (III).

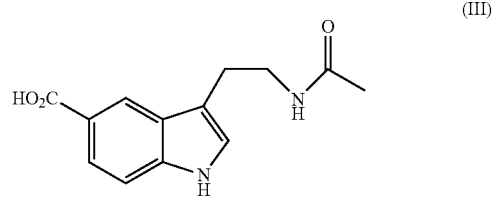 [SMILES: CC(=O)NCCc1c[nH]c2ccc(C(=O)O)cc12]

(III)

Examples of analogues of melatonin include 2-iodomelatonin, 6-chloromelatonin, 6,7-dichloro-2-methylmelatonin and 8-hydroxymelatonin, all of which contain the 5-methoxy indole ring as an essential moiety (Dubocovich, et al. *Proc. Nat'l. Acad. Sci.* (USA) 1987, 84, 3916-3918; Dubocovich, M; *J. Pharmacol. Exp. Ther:* 1985, 234, 395; Dubocovich, M. *L. Trends Pharmacol. Sci.* 1995, 16, 50-56).

According to one aspect of the invention, the paclitaxel comprises one or more analogues of paclitaxel optionally in combination with paclitaxel.

According to another aspect of the invention, the melatonin comprises one or more analogues of melatonin optionally in combination with melatonin.

Owing to the properties of proliferating SMCs, the inventors find that a composition comprising combinations of analogues may also be effective at reducing a proliferating cell mass.

Stereoisomer, tautomers, racemates, prodrugs, metabolites, pharmaceutically acceptable salts, bases, esters, structurally related compounds or solvates of paclitaxel or melatonin are within the scope of the invention, unless otherwise stated.

The pharmaceutically acceptable salts of paclitaxel or melatonin according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such a sarginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The term "stereoisomer", as used herein, defines all possible compounds made up of the same atoms bonded by the same sequence of bonds but having different three-dimensional structures which are not interchangeable, which paclitaxel or melatonin may possess. Unless otherwise mentioned or indicated, the chemical designation of paclitaxel or melatonin herein encompasses the mixture of all possible stereochemically isomeric forms, which said compound may possess. Said mixture may contain all diastereomers and/or enantiomers of the basic molecular structure of said compound. All stereochemically isomeric forms of paclitaxel or melatonin either in pure form or in admixture with each other are intended to fall within the scope of the present invention.

Paclitaxel or melatonin may also exist in their tautomeric forms. Such forms, although not explicitly indicated in the compounds described herein, are intended to be included within the scope of the present invention.

For therapeutic use, the salts of paclitaxel or melatonin according to the invention are those wherein the counter-ion is pharmaceutically or physiologically acceptable.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active paclitaxel or melatonin in vivo.

When the composition comprises a combination of melatonin and paclitaxel, said composition may be provided on the balloon such that the melatonin is separately or simultaneously administered to the subject with respect to the paclitaxel.

By simultaneous administration it is meant the melatonin and paclitaxel are administered to a subject at the same time. For example, balloon may be provided with a composition comprising a mixture melatonin and paclitaxel.

By separate administration it is meant that the melatonin and paclitaxel are separately administered to a subject at the same time or substantially the same time. The components are present on the balloon as separate, unmixed preparations. For example, the balloon may be provided with a layer comprising paclitaxel and a separate layer comprising melatonin. The paclitaxel and melatonin respective layers do not intermix on the balloon prior to administration, thereby giving rise to separately administered compounds.

The maximum thickness of a separately administered paclitaxel layer may be 0.007 mm, 0.008 mm, 0.009 mm, 0.01 mm, 0.012 mm, 0.014 mm, 0.016 mm, 0.018 mm, 0.02 mm, 0.03 mm, 0.04 mm, 0.06 mm, 0.08 mm, 0.09 mm, 0.10 mm, 0.15 mm or 0.20 mm, or a value in the range between any two of the aforementioned values, preferably between 0.007 to 0.1 mm, more preferably between 0.009 to 0.03 mm.

The maximum thickness of a separately administered melatonin layer may be 0.007 mm, 0.008 mm, 0.009 mm, 0.01 mm, 0.012 mm, 0.014 mm, 0.016 mm, 0.018 mm, 0.02 mm, 0.03 mm, 0.04 mm, 0.06 mm, 0.08 mm, 0.09 mm, 0.10 mm, 0.15 mm or 0.20 mm, or a value in the range between any two of the aforementioned values, preferably between 0.007 to 0.1 mm, more preferably between 0.009 to 0.03 mm.

According to one aspect of the invention, the separate layers of paclitaxel and melatonin are disposed one over the other, so that an outer layer is first administered followed by an inner layer in situ. "Inner layer" and "outer layer" refer to the relative positions of the layers, one over the other, with respect to the balloon. The inner layer is the layer of the two, closer to the balloon surface, and may or may not be the innermost layer. For example, the balloon may first be coated with an innermost layer of hydrophilic substance to which the inner layer can attach. The outer layer is positioned at least partially over the inner layer. It is the layer of the two layers, further from the balloon surface; it will be the layer of the two layers, initially closer to the site of administration. The outer layer may or may not be the outermost layer. For example, the balloon may optionally be further coated with a layer of polymer or other additional consecutive separate layers of paclitaxel and melatonin for example whereby the final coating forms the outermost layer. One or more intervening layers may be present between the inner and outer layers. According to one aspect of the invention, one or more intervening layers comprises polymer (e.g. controlled release polymer). Alternatively, no intervening layers may be present between the inner and outer layers.

According to one aspect of the invention, an inner layer comprises paclitaxel and an outer layer comprises melatonin. In a preferred embodiment, an inner layer comprises paclitaxel devoid of any polymer (e.g. devoid of a controlled release polymer) and an outer layer comprises melatonin. In a more preferred embodiment, an inner layer comprises paclitaxel devoid of any polymer (e.g. devoid of a controlled release polymer), and an outer layer comprises melatonin and polymer (e.g. controlled release polymer). In a preferred embodiment, an inner layer comprises paclitaxel devoid of any polymer (e.g. devoid of a controlled release polymer), an outer layer comprises melatonin devoid of any polymer (e.g. devoid of a controlled release polymer), and outermost layer comprises polymer (e.g. controlled release polymer). The layers are distinct, separate and do not intermix in the undeployed balloon.

Such balloons are prepared by applying a first coating (e.g. paclitaxel devoid of polymer), allow the coating to dry, and applying a second coating (e.g. melatonin devoid of polymer) and allowing the second coating to dry. Subsequent layers (e.g. controlled release polymer) are applied using similar steps of application and drying to ensure the respective coatings do not mix.

According to one aspect of the invention, the separate layers of paclitaxel and melatonin are provided at different locations on the balloon thereby achieving physical (spatial) separation. According to one embodiment of the invention, a balloon is provided with a plurality of discrete depositions of paclitaxel and a plurality of discrete depositions of melatonin, wherein the respective depositions do not overlap. Preferably the number of respective discrete depositions is equal for a given area of balloon.

According to one embodiment of the invention, a balloon may be provided with a plurality of deposited paclitaxel-comprising strips, interlaced with a plurality of similarly deposited melatonin-comprising strips, which strips do not overlap. The strips may be aligned along the longitudinal axis of the balloon, perpendicular to the longitudinal axis of the balloon or at an angle thereto. The ratio of melatonin:paclitaxel strips may be 0.60, 0.80, 1.00, 1.50, 2.00, 3.00, 4.00, 5.00, 6.00 or 7.00:1 or a value in the range between any two of the aforementioned values, preferably 3.00 to 5.00:1.

According to one particular embodiment, a balloon of the invention may be provided with a plurality of paclitaxel-comprising spots wherein at least part of a space between the spots is provided with a melatonin-comprising spot, where the respective spots do not overlap. The ratio of melatonin:paclitaxel spots may be 0.60, 0.80, 1.00, 1.50, 2.00, 3.00, 4.00, 5.00, 6.00 or 7.00:1 or a value in the range between any two of the aforementioned values, preferably 3.00 to 5.00:1.

In a preferred aspect, one set of discrete depositions comprises paclitaxel and another set of discrete depositions melatonin. In a more preferred embodiment, one set of discrete depositions comprises paclitaxel devoid of any polymer (e.g. controlled release polymer) and another set of discrete depositions comprises melatonin. In a most preferred embodiment, one set of discrete depositions comprises paclitaxel devoid of any polymer (e.g. controlled release polymer) and another set of discrete depositions comprises melatonin, and a distinct and separate layer of polymer (e.g. controlled release) is provided covering both set of spots.

The medical uses of the composition described below, also apply to the composition comprising melatonin and paclitaxel, for simultaneous, separate or sequential administration to a subject as disclosed here above.

A composition of the invention may comprise additional substances, such as, for example, those that facilitate sobulisation of the melatonin and paclitaxel and/or the attachment of the melatonin and paclitaxel to the balloon, and those that facilitate the functioning or the performance of the balloon in situ. Such additional substances are known to the skilled artisan.

As mentioned elsewhere, it is an aspect of the invention that the composition may further comprise a polymer. A polymer according to the present invention is any that facilitates attachment of the medicament to the balloon and/or facilitates the controlled release of medicament. Preferably, the polymer is used to tune the release of medicament to obtain an optimal response; in words, to control the rate at which the medicament is released from the balloon. A too fast release of the medicament could result in vessel wall toxicity. By tuning the release, and the vessel wall is impregnated for a certain time period (e.g. minutes or seconds) with the composition resulting in an optimal effect. The skilled person will understand that the type of polymer, concentration, thickness can be adjusted within the routine practices of the skilled person to obtain an optimum release.

Polymers suitable for use in the present invention are any that are capable of attaching to the balloon and releasing medicament. They must be biocompatible to minimize irritation to the vessel wall. Polymers may be, for example, film-forming polymers that are absorbable or non-absorbable. The polymer may be biostable or bioabsorbable depending on the desired rate of release or the desired degree of polymer stability.

Suitable bioabsorbable polymers that could be used include polymers selected from the group consisting of aliphatic polyesters, poly(amino acids), copoly(ether-esters), polyalkylenes oxalates, polyamides, poly(iminocarbonates), polyanhydrides, polyorthoesters, polyoxaesters, polyamidoesters, polylactic acid (PLA), polyethylene oxide (PEO), polycaprolactone (PCL), polyhydroxybutyrate valerates, polyoxaesters containing amido groups, poly(anhydrides), polyphosphazenes, silicones, hydrogels, biomolecules and blends thereof. Another polymer is any poly(ester amide).

For the purpose of the present invention, aliphatic polyesters include homopolymers and copolymers of lactide (which includes lactic acid D-, L- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein).

Polyphosphazenes, co-, ter- and higher order mixed monomer based polymers made from L-lactide, D,L-lactide, lactic acid, glycolide, glycolic acid, para-dioxanone, trimethylene carbonate and epsilon-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein).

Polyanhydrides from diacids of the form HOOC—$C_6H_4$—O—$(CH_2)$m-O—$C_6H_4$—COOH wherein m is an integer in the range of from 1 to 11, 3 to 9, 3 to 7, 2 to 6 or preferably 2 to 8, and copolymers thereof with aliphatic alpha-omega diacids of up to 8, 9, 10, 11 or preferably 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583; (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference).

Suitable biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the balloon. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e. carboxymethyl cellulose and hydoxyalkyl celluloses); and combinations thereof. Polyamides for the purpose of this application would also include polyamides of the form-NH—($CH_2$)n-CO— and NH—($CH_2$)x-NH—CO—($CH_2$)y-CO, wherein n is an integer in from 5 to 15, 7 to 11, 8 to 10 or preferably 6 to 13;

x is an integer in the range of from 5 to 14, 7 to 11, 8 to 10 or preferably 6 to 12; and y is an integer in the range of from 3 to 18, 5 to 14, 6 to 10 or preferably 4 to 16. The list provided above is illustrative but not limiting.

Other polymers suitable for use in the present invention are bioabsorbable elastomers, more preferably aliphatic polyester elastomers. In the proper proportions aliphatic polyester copolymers are elastomers. Elastomers present the advantage that they tend to adhere well to the balloon and can withstand significant deformation without cracking. The high elongation and good adhesion provide superior performance to other polymer coatings when the coated balloon is expanded. Examples of suitable bioabsorbable elastomers are described in U.S. Pat. No. 5,468,253 hereby incorporated by reference. Preferably the bioabsorbable biocompatible elastomers based on aliphatic polyester, including but not limited to those selected from the group consisting of elastomeric copolymers of epsilon-caprolactone and glycolide (preferably having a mole ratio of epsilon-caprolactone to glycolide of from about 35:65 to about 65:35, more preferably 45:55 to 35:65) elastomeric copolymers of E-caprolactone and lactide, including L-lactide, D-lactide blends thereof or lactic acid copolymers (preferably having a mole ratio of epsilon-caprolactone to lactide of from about 35:65 to about 90:10 and more preferably from about 35:65 to about 65:35 and most preferably from about 45:55 to 30:70 or from about 90:10 to about 80:20) elastomeric copolymers of p-dioxanone (1,4-dioxan-2-one) and lactide including L-lactide, D-lactide and lactic acid (preferably having a mole ratio of p-dioxanone to lactide of from about 30:70 to about 70:30, 45:55 to about 55:45, and preferably from about 40:60 to about 60:40) elastomeric copolymers of epsilon-caprolactone and p-dioxanone (preferably having a mole ratio of epsilon-caprolactone to p-dioxanone of from about 40:60 to about 60:40 and preferably from about 30:70 to about 70:30) elastomeric copolymers of p-dioxanone and trimethylene carbonate (preferably having a mole ratio of p-dioxanone to trimethylene carbonate of from about 40:60 to about 60:40, and preferably from about 30:70 to about 70:30), elastomeric copolymers of trimethylene carbonate and glycolide (preferably having a mole ratio of trimethylene carbonate to glycolide of from about 40:60 to about 60:40 and preferably from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. As is well known in the art these aliphatic polyester copolymers have different hydrolysis rates, therefore, the choice of elastomer may in part be based on the requirements for the coatings adsorption. For example epsilon-caprolactone-co-glycolide copolymer (45:55 mole percent, respectively) films lose 90% of their initial strength after 2 weeks in simulated physiological buffer whereas the epsilon-caprolactone-co-lactide copolymers (40:60 mole percent, respectively) loses all of its strength between 12 and 16 weeks in the same buffer. Mixtures of the fast hydrolyzing and slow hydrolyzing polymers can be used to adjust the time of strength retention.

The amount of coating may range from about 0.1 to about 20 as a percent of the total weight of the balloon after coating and preferably will range from about 0.5 to about 15 percent. The polymer coatings may be applied in one or more coating steps depending on the amount of polymer to be applied. Different polymers may also be used for different layers in the balloon coating. In fact it may be an option to use a dilute first coating solution as primer to promote adhesion of a subsequent coating layers that may contain medicament.

Additionally, a top coating can be applied to further delay release of medicament, or it could be used as the matrix for the delivery of a different pharmaceutically active material. The amount of top coatings on the balloon may vary, but will generally be less than about 2000 micrograms, preferably the amount of top coating will be in the range of about 1 micrograms to about 1700 micrograms and most preferably in the range of from about 100 micrograms to 1000 about micrograms. Layering of coating of fast and slow hydrolyzing copolymers can be used to stage release of the drug or to control release of different agents placed in different layers. Polymer blends may also be used to control the release rate of different agents or to provide desirable balance of coating (i.e. elasticity, toughness etc.) and drug delivery characteristics (release profile). Polymers with different solubilities in solvents can be used to build up different polymer layers that may be used to deliver different drugs or control the release profile of a drug. For example since epsilon-caprolactone-co-lactide elastomers are soluble in ethyl acetate and epsilon-caprolactone-co-glycolide elastomers are not soluble in ethyl acetate. A first layer of epsilon-caprolactone-co-glycolide elastomer containing a drug can be over coated with epsilon-caprolactone-co-glycolide elastomer using a coating solution made with ethyl acetate as the solvent. Additionally, different monomer ratios within a copolymer, polymer structure or molecular weights may result in different solubilities. For example, 45/55 epsilon-caprolactone-co-glycolide at room temperature is soluble in acetone whereas a similar molecular weight copolymer of 35/65 epsilon-caprolactone-co-glycolide is substantially insoluble within a 4 weight percent solution. The second coating (or multiple additional coatings) can be used as a top coating to delay the drug delivery of the drug contained in the first layer. Alternatively, the second layer could contain another medicament to provide for sequential delivery. Multiple layers of could be provided by alternating layers of first one polymer then the other. As will be readily appreciated by those skilled in the art numerous layering approaches can be used to provide the desired drug delivery.

The coatings can be applied by suitable methodology known to the skilled person, such as, for example, dip coating, spray coating, electrostatic coating, melting a powdered form onto the balloon.

Other examples of polymeric coatings, and coating methods are given in patent documents EP 1 107 707, WO 97/10011, U.S. Pat. No. 6,656,156, EP 0 822 788, U.S. Pat. No. 6,364,903, U.S. Pat. No. 6,231,600, U.S. Pat. No. 5,837,313, WO 96/32907, EP 0 832,655, U.S. Pat. No. 6,653,426, U.S. Pat. No. 6,569,195, EP 0 822 788 B1, WO 00/32238, U.S. Pat. No. 6,258,121, EP 0 832,665, WO 01/37892, U.S. Pat. No. 6,585,764, U.S. Pat. No. 6,153,252 which are incorporated herein by reference.

The medicament disposed on the balloon is present in an amount for the treatment of tissues and cells present in the cavity. The size of balloon and concentration of composition thereon can be calculated using known techniques by the skilled person.

Where the medicament is suitable for the treatment of stenosis or restenosis, for instance, it is preferably present in an amount to inhibit proliferation of smooth muscle cells. It is preferably present in an amount to prevent or treat stenosis or restenosis.

An amount of medicament such as paclitaxel and/or melatonin that is effective to prevent or treat stenosis or restenosis is an amount that is effective to ameliorate or minimise the clinical impairment or symptoms of the stenosis or restenosis. For example, the clinical impairment or symptoms of stenosis or restenosis may be ameliorated or minimised by diminishing any pain or discomfort suffered by the subject; by extending the survival of the subject beyond that which would otherwise be expected in the absence of such treatment; by inhibiting or preventing the development or spread of stenosis or restenosis; or by limiting, suspending, terminating, or otherwise controlling the maturation and proliferation of cells in stenosis or restenosis.

The size of balloon and concentration of composition thereon will vary depending on the particular factors of each case, including the type of stenosis or restenosis, the stage of stenosis or restenosis. These amounts can be readily determined by the skilled artisan.

According to one aspect of the invention, a balloon is coated with a composition comprising paclitaxel such that the paclitaxel concentration delivered to a subject is greater than or equal to 0.00001, 0.00005, 0.0001, 0.0002, 0.0004, 0.0006, 0.0008, 0.001, 0.002, 0.003, 0.004, 0.005, 0.006, 0.007, 0.008, 0.009, 0.01, 0.05, 0.1, 0.5, 0.75 1, 1.5, 3, 4.5, 5, 9, 10, 20, 40, 60, 80, or 100 micrograms paclitaxel/mm$^2$ of balloon, or a concentration in the range between any two of the aforementioned values inclusive.

According to another aspect of the invention, a balloon is coated with a composition comprising melatonin such that the melatonin concentration delivered to a subject is greater than or equal to 0.00001, 0.00005, 0.0001, 0.0002, 0.0004, 0.0006, 0.0008, 0.001, 0.002, 0.003, 0.004, 0.005, 0.006, 0.007, 0.008, 0.009, 0.01, 0.05, 0.1, 0.5, 1, 5, 10, 20, 40, 60, 80 or 100 micrograms melatonin/mm$^2$ of balloon, or a concentration in the range between any two of the aforementioned values inclusive.

The concentration of melatonin and/or paclitaxel per mm$^2$ of balloon required to arrive at the above doses can be readily calculated by the skilled person.

According to one aspect of the invention, the concentration of melatonin present on a balloon may be between 0.001 and 15, 0.005 and 10, 0.02 and 5, or 0.1 and 2 micrograms inclusive melatonin/mm$^2$; preferably it is between 0.005 and 10 micrograms inclusive melatonin/mm$^2$ of balloon.

According to another aspect of the invention, the concentration of paclitaxel on a balloon may be between 0.0001 and 0.05, 0.0005 and 0.5, or 0.001 and 5 micrograms inclusive paclitaxel/mm$^2$; preferably it is between 0.001 and 5 micrograms inclusive paclitaxel/mm$^2$.

Where both paclitaxel and melatonin are present together, the concentration of paclitaxel on a balloon is lower than the concentration of melatonin. The concentration of paclitaxel may be equal to or less than 0.95, 0.9, 0.85, 0.8, 0.75, 0.7, 0.65, 0.6, 0.55, 0.50, 0.45, 0.40, 0.35, 0.30, 0.2, 0.1, 0.05 times the concentration of melatonin, or may be a fraction of the melatonin concentration which fraction is in the range between any two of the aforementioned values inclusive. Preferably it is between 0.1 to 0.3 times the concentration of melatonin. Experiments by the present inventors indicate inhibition occurs with 0.885 micrograms melatonin/mm$^2$ balloon with a paclitaxel concentration of 0.118 micrograms/mm$^2$ balloon.

The composition may comprise additives to facilitate storage, dissolubility and application of the medicament, for instance, salts, buffers, gels, surfactants, etc. Biocompatible coating or adhesive agents may be added. Under ordinary conditions of storage and use, these compositions may contain a preservative to prevent the growth of microorganisms.

Examples of conditions treatable using the present invention include, but are not limited to stenosis, restenosis, tumourous growths, infections, and inflammations. Examples of tumours suitable for treatment according to the invention include, but are not limited to biliary tract adenocarcinoma, esophageal epidermoid or adenocarcinoma, colon and rectum adenocarcinoma, bronchial epidermoid or adeno-carcinomas, uterine. The medicament may useful for shrinking a mass of proliferating cells or may completely eradicate it. The treatment of proliferating cells or tissues may also be applied to regions from which a proliferating mass has been surgically removed to reduce the possibility of relapse or regrowth. The treatment can also be the prevention of regrowth.

A subject according to the present invention may be any living body susceptible to treatment by the balloon. Examples include, but are not limited to humans, livestock, domestic animals, wild animals, or any animal in need of treatment. Examples of an animal is human, horse, cat, dog, mice, rat, gerbil, bovine species, pig, fowl, camelidae species, goat, sheep, rabbit, hare, bird, elephant, monkey, chimpanzee etc. An animal may be a mammal.

One embodiment of the invention is a process for obtaining a composition-eluting balloon catheter 100 having a proximal 20 and distal 15 end, comprising an elongated catheter tube 6 with an inflation lumen 7 extending therewithin and at least one inflatable balloon (4 having a central longitudinal balloon axis B-B' towards the distal end 15 in fluid communication with the inflation lumen 7, wherein the balloon 4 in the uninflated condition is configured as a plurality of folded wings 10', 10", comprising the steps:

a) applying the composition 12', 12" at least partially over one or both surfaces of the balloon wing;

b) folding the balloon wings 10', 10" around the central longitudinal balloon axis B-B' such that applied composition 12', 12" is disposed within the folds of the wings;

c) removing excess composition 12', 12" from the surface of the folded balloon; and d) applying a relief structure 30 to the balloon 4 in the folded condition, comprising at least one groove on the outside of the plurality of folded wings 10', 10", configured to substantially reduce in depth in an inflated state of the balloon 4, which at least one groove is essentially devoid of composition 12', 12".

According to one aspect of the process, one or both surfaces of the balloon wings 10', 10" may be at least partially coated with a hydrophilic coating, prior to application of the composition.

According to one aspect of the process, the composition (12', 12") may be applied in a solution of organic solvent preferably methanol, propanol, acetone, or ethyl acetate, more preferably ethanol, at least partially over the coated surface.

According to one aspect of the process, the relief structure has one or more of the features describe above in respect of the relief structures.

Another embodiment of the invention is a composition-eluting balloon catheter 100 obtainable or obtained by a process as described above. The balloon catheter may be a rapid exchange catheter or an over the wire catheter.

Examples

1. Balloon Preparation

A balloon was prepared by coating the outer surface with a PVP hydrophilic substance, then over-coating the hydrophilic substance with paclitaxel (PTX) and allowing the coating to dry. The paclitaxel was disposed exclusively between the balloon folds and at a concentration of 1.5 µg/mm$^2$.

2. Retention Property of Hydrophilic Coating in Water (In Vitro)

A balloon was prepared according to experiment 1. In the uninflated state, the balloon was passed three times through a guiding catheter and coronary model in a water bath at 37 deg C. Analysis of the amount of paclitaxel remaining on the balloon indicated a reduction of less than 1% of the total load.

3. Retention Property of Hydrophilic Coating in an Ex Vivo Model Living Porcine Artery Three balloons were prepared according to experiment 1, having a concentration of paclitaxel of 0.75 µg/mm$^2$, 1.5 µg/mm$^2$ and 4.5 µg/mm$^2$. Each balloon was placed in ex vivo model living porcine artery forming a closed loop model. Concentration of paclitaxel dispersed in the system prior to inflation were measured, and the results are given in Table 1 below. The systemic effect of paclitaxel in the blood stream at the concentrations cited is negligible.

TABLE 1

Blood concentration of paclitaxel on the balloon before inflation in an ex vivo model living porcine artery.

| Concentration paclitaxel (PTX) on balloon | Concentration paclitaxel (PTX) in blood before inflation (µM) |
|---|---|
| DEB-Y: 1.5 µg/mm$^2$ | 0.005 |
| DEB-Y/2: 0.75 µg/mm$^2$ | 0.018 |
| DEB-3Y: 4.5 µg/mm$^2$ | 0.002 |

4. Integrity of Hydrophilic Coating (In Vitro)

A balloon was prepared according to experiment 1. The balloon was repeatedly inflated and deflated in both wet and dry conditions, and visually inspected for cracking or other changes to the integrity of the surface. There was no cracking of the coating that could lead to particle release when the surface was analysed at 300× magnification.

5. Effect of Radiation Sterilization

A balloon was prepared according to experiment 1. The balloon was sterilized by irradiation with a gamma-ray source under standard conditions. Analysis by HPLC of the paclitaxel on the balloon indicated a variation in paclitaxel of less than 3% between repeated products tested.

6. Concentration on Balloon Vs Concentration Administered (Ex Vivo)

Figure 6:
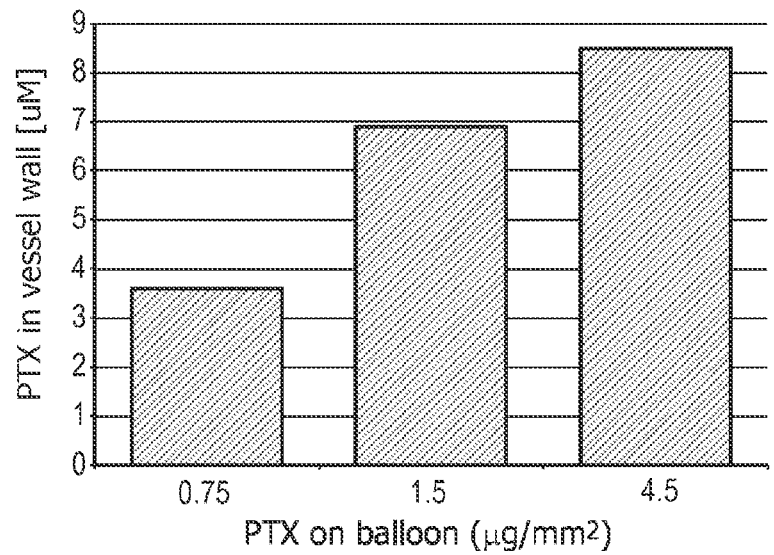
FIG. 6 Graph depicting the results of experiment 6 i.e. paclitaxel dose delivered to the arterial wall as a function of paclitaxel (PTX) concentration on the balloon.

Three balloons were prepared according to experiment 1, having a concentration of paclitaxel of 0.75 µg/mm$^2$, 1.5 µg/mm$^2$ and 4.5 µg/mm$^2$. Each was inserted into an ex vivo model living porcine artery, and inflated for 30 seconds. The dose of paclitaxel delivered to the arterial wall was measured. The result shown in FIG. 6, reveals that dose administered is approximately directly proportional to the concentration of paclitaxel on the balloon. It is noted that after leaving the balloon in the blood stream for 2.5 minutes in a non-inflated condition, less than 3.5% of the total load was detected in the blood stream.

7. Multiple Dose Administrations at the Same Location (Ex Vivo)

Figure 7:
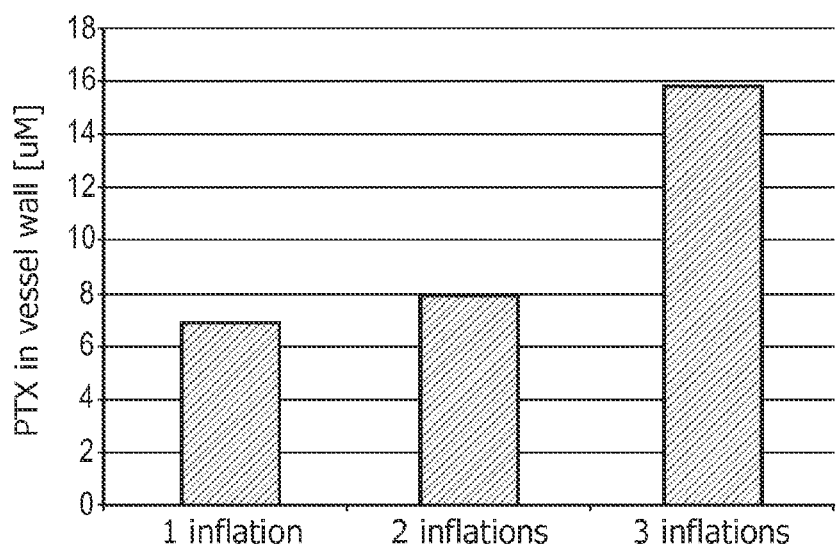
FIG. 7 Graph depicting the results of experiment 7 i.e. paclitaxel dose delivered to the arterial wall as a function of multiple inflations at the same location.

A balloon was prepared according to experiment 1. It was inserted into an ex vivo model living porcine artery, and inflated for 30 seconds then deflated. This was repeated a further 2 times in the same location. The dose of paclitaxel delivered to the arterial wall was measured after each deflation. The result shown in FIG. 7, reveals that dose administered to the wall increases with each inflation i.e. there is a cumulative effect.

8. Multiple Dose Administrations at Different Location (Ex Vivo)

Figure 8:
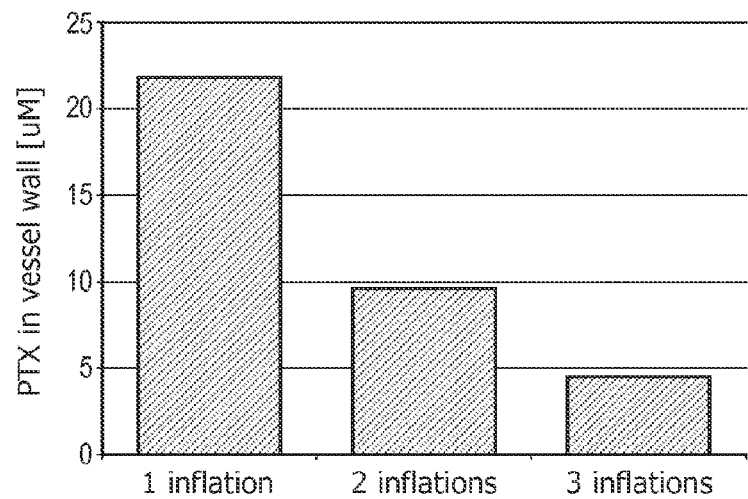
FIG. 8 Graph depicting the results of experiment 8 i.e. paclitaxel dose delivered to the arterial wall as a function of multiple inflations to different locations.

A balloon was prepared according to experiment 1. It was inserted into an ex vivo model living porcine artery, and inflated for 30 seconds then deflated. This was repeated a further 2 times at different locations. The dose of paclitaxel delivered to the arterial wall was measured after each deflation. The result shown in FIG. 8, reveals that the balloon delivers paclitaxel after each inflation, with decreasing concentration.

9. Dose Administered Vs Time (Ex Vivo)

A balloon was prepared according to experiment 1. It was inserted into an ex vivo model living porcine artery, and inflated for 15, 30, 60, or 120 seconds then deflated. The dose of paclitaxel delivered to the arterial wall was measured after deflation. The result shown in FIG. 9, reveals that the concentration of paclitaxel delivered to the vessel wall after each inflation is essentially directly proportional with inflation time.

10. Four Week Quantitative Coronary Angiography (In Vivo)

Three balloons were prepared according to experiment 1, having a concentration of paclitaxel of 0.75 µg/mm$^2$, 1.5 µg/mm$^2$ and 4.5 µg/mm$^2$. The balloons were used in an in vivo Quantitative Coronary Angiography (QCA). The results of the QCA are shown in Tables 2 to 4 below. For comparison, the results of a trial of B.Braun SeQuent Please paclitaxel drug eluting balloon are given in Table 5.

TABLE 2

Results of four week porcine in vivo Quantitative Coronary Angiography (QCA) using balloon of the invention.

| Balloon paclitaxel concentration | PRE VD (mm) | POST MLD (mm) | FUP MLD (mm) | FUP RD (mm) | FUP % DS (%) | LLL (mm) |
|---|---|---|---|---|---|---|
| DEB-Y: 1.5 µg/mm² | 2.45 | 3.12 | 3.15 | 3.29 | 4.15 | −0.03 |
| DEB-Y/2: 0.75 µg/mm² | 2.47 | 3.15 | 2.97 | 3.11 | 4.95 | 0.18 |
| DEB-3Y: 4.5 µg/mm² | 2.38 | 3.06 | 2.78 | 3.11 | 12.22 | 0.28 |

KEY: PRE—prior to treatment; POST—after treatment; FUP—follow up; LLL—late luminal loss; VD—vessel diameter; MLD—minimum lumen diameter; RD—reference diameter; % DS—percentage diameter stenosis.

According to the results of Table 2, at least the FUP % DS and LLL indicates that all doses are effective, 1.5 µg/mm² (DEB-Y) being the most effective dose.

TABLE 3

Histology analysis after four week porcine in vivo Quantitative Coronary Angiography (QCA) using balloon of the invention.

| Balloon paclitaxel concentration | Injury score | Fibrin score | Inflam. score | Endothelialization (complete) |
|---|---|---|---|---|
| DEB-Y: 1.5 µg/mm² | 0.5 | 0.04 | 0.15 | 88.9% |
| DEB-Y/2: 0.75 µg/mm² | 0.91 | 0.26 | 0.59 | 77.8% |
| DEB-3Y: 4.5 µg/mm² | 0.98 | 0.30 | 0.81 | 59.3% |

According to the results of Table 3, at least the Inflammation Score indicates that all doses are effective, 1.5 µg/mm² (DEB-Y) being the most effective dose.

TABLE 4

Histo-morphometry analysis after four week porcine in vivo Quantitative Coronary Angiography (QCA) using balloon of the invention.

| Balloon paclitaxel concentration | Lumen area (mm²) | Neointimal area (mm²) | IEL area (mm²) | Media area (mm²) | EEL area (mm²) | % Area stenosis (%) | Max. Neointimal Thickness (mm) |
|---|---|---|---|---|---|---|---|
| DEB-Y: 1.5 µg/mm² | 3.23 | 0.16 | 3.39 | 1.07 | 4.46 | 5.40 | 0.02 |
| DEB-Y/2: 0.75 µg/mm² | 2.43 | 0.32 | 2.75 | 0.91 | 3.67 | 12.10 | 0.06 |
| DEB-3Y: 4.5 µg/mm² | 2.20 | 0.44 | 2.64 | 1.10 | 3.75 | 19.60 | 0.10 |

KEY: IEL area—internal elastic lamina area; EEL—external elastic lamina area.

According to the results of Table 4, at least the % area stenosis indicates that all doses are effective, 1.5 µg/mm² (DEB-Y) being the most effective dose.

TABLE 5

B. Braun SeQuent Please paclitaxel eluting balloon, published human trial data.

| Study | Set Up | n = | [paclitaxel] | Mace | LLL |
|---|---|---|---|---|---|
| Pep Cad I | Small Vessels | 120 | 3 µm/mm² | 15% | 0.32 |
| Pep Cad II | In-Stent SeQuent ® | 66 | 3 µm/mm² | 7.8% | 0.20 |
| | In-Stent Taxus | 65 | 3 µm/mm² | 16.9% | 0.45 |
| Pep Cad III | De-Novo SeQuent ® + Stent | 312 | 3 µm/mm² | 13.8% | 0.41 |
| | DeNovo Cypher | 325 | 3 µm/mm² | 6.9% | 0.16 |

KEY:
"n"—number of experiments;
Mace—major adverse cardiac events;
LLL—Late luminal loss.

According to the results of Table 5, the effect of the hydrophobic coating of the present invention provides a late luminal loss effect at least the same as existing products, with the advantages of controlled and reduced systemic release.

11. Concentration on Balloon with Stent Vs Concentration Administered (Ex Vivo)

Figure 10:
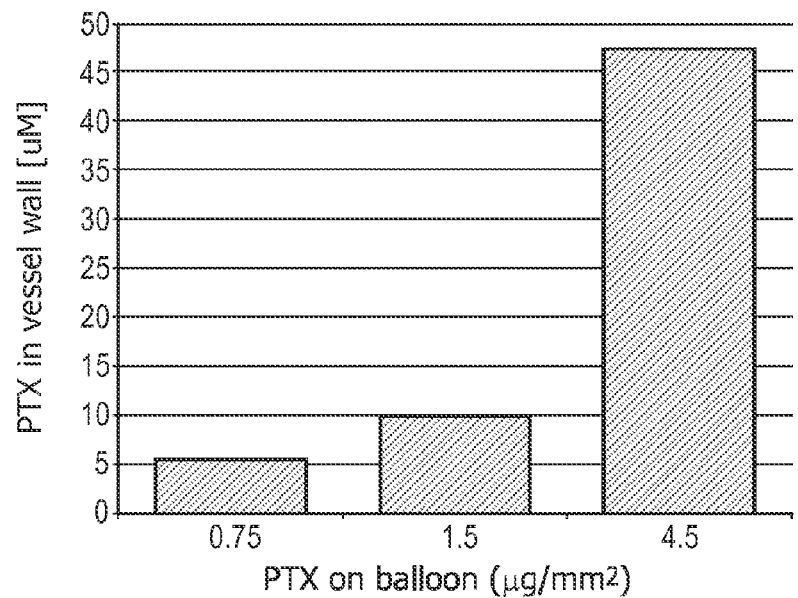
FIG. 10 Graph depicting the results of experiment 11 i.e. paclitaxel dose delivered to the arterial wall as a function of paclitaxel (PTX) concentration on the balloon disposed with a stent.

Balloons with three different concentrations were prepared according to experiment 1, having a concentration of paclitaxel of 0.75 µg/mm², 1.5 µg/mm² and 4.5 µg/mm², and provided with a non-drug eluting stent of cobalt-chromium alloy (F562). Each was inserted into an ex vivo model living porcine artery, and inflated for 30 seconds, after which time the stent was deployed. The dose of paclitaxel delivered to the arterial wall was measured. The result shown in FIG. 10, reveals that dose administered is approximately proportional to the concentration of paclitaxel on the balloon. It is noted that after leaving the uninflated balloon in the blood stream for 2.5 minutes, no paclitaxel was detected in the blood stream.

12. Multiple Dose Administrations of Balloon with Stent at the Same Location (Ex Vivo)

Figure 11:
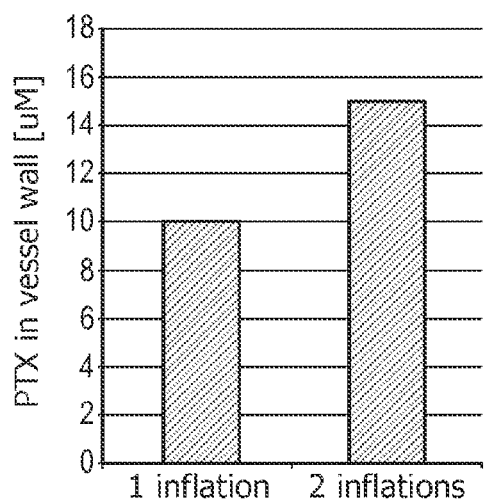
FIG. 11 Graph depicting the results of experiment 12 i.e. paclitaxel dose delivered to the arterial wall as a function of multiple inflations at the same location; the balloon is disposed with a stent.

A balloon was prepared according to experiment 1 and provided with a non-drug eluting stent of cobalt-chromium alloy (F562). It was inserted into an ex vivo model living porcine artery, and inflated for 30 seconds then deflated; after inflation the stent was deployed. This was repeated a further 2 times in the same location. The dose of paclitaxel delivered to the arterial wall was measured after each deflation. The result shown in FIG. 11, reveals that dose administered to the wall increases with each inflation i.e. there is a cumulative effect.

13. Dose Administered of Balloon with Stent Vs Time (Ex Vivo)

Figure 9:
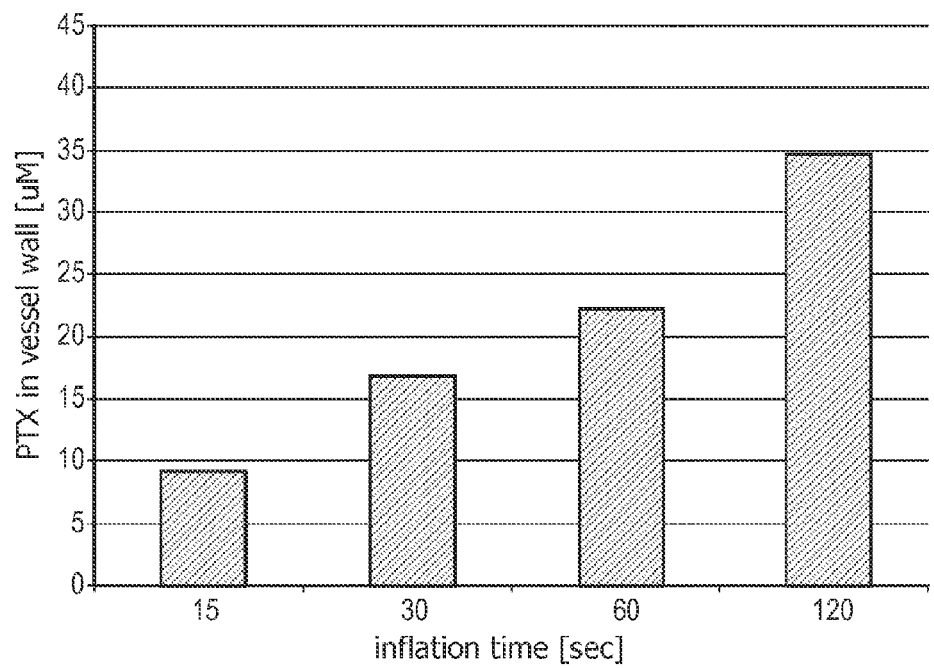
FIG. 9 Graph depicting the results of experiment 9 i.e. paclitaxel dose delivered to the arterial wall as a function of inflation time.
Figure 12:
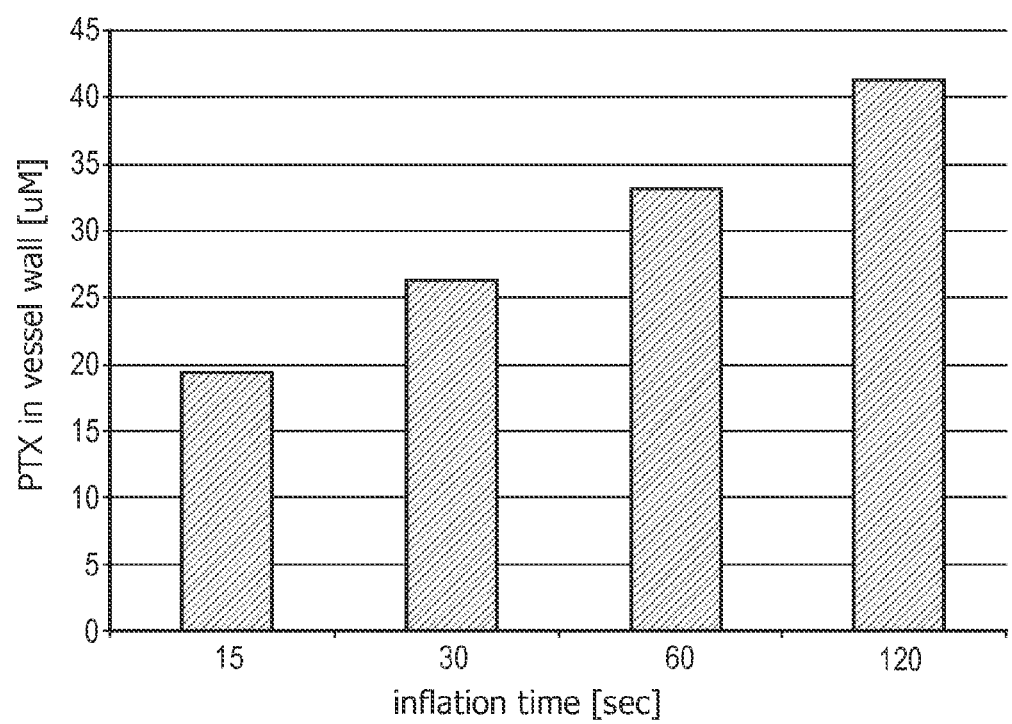
FIG. 12 Graph depicting the results of experiment 9 i.e. paclitaxel dose delivered to the arterial wall as a function of inflation time; the balloon is disposed with a stent.

A balloon was prepared according to experiment 1 with a non-drug eluting stent of cobalt-chromium alloy (F562). It was inserted into an ex vivo model living porcine artery, and inflated for 15, 30, 60, or 120 seconds then deflated; after inflation the stent was deployed. The dose of paclitaxel delivered to the arterial wall was measured after deflation. The result shown in FIG. 12, reveals that the concentration of paclitaxel delivered to the vessel wall after each inflation is essentially directly proportional with inflation time. It is noted that the amount delivered is greater compared with the balloon alone (FIG. 9).

14. Four Week Quantitative Coronary Angiography (In Vivo) with Stent

Three balloons were prepared according to experiment 1, but having a concentration of paclitaxel of 0.75 µg/mm$^2$, 1.5 µg/mm$^2$ and 4.5 µg/mm$^2$, and each disposed with a non-drug eluting stent of cobalt-chromium alloy (F562). The balloons were used in an in vivo Quantitative Coronary Angiography (QCA). The results of the QCA are shown in Table 6 below. A dose effect is significant.

TABLE 6

Results of four week porcine in vivo Quantitative Coronary Angiography (QCA) using balloon of the invention + non drug-eluting stent.

| Balloon paclitaxel concentration | PRE VD (mm) | POST MLD (mm) | FUP MLD (mm) | FUP RD (mm) | FUP % DS (%) | LLL (mm) |
|---|---|---|---|---|---|---|
| CoCr | 2.64 | 3.09 | 2.15 | 3.15 | 32.4 | 0.92 |
| CoCr DEB-Y: 1.5 µg/mm$^2$ | 2.61 | 3.04 | 2.20 | 3.29 | 28.2 | 0.84 |
| CoCr DEB-Y/2: 0.75 µg/mm$^2$ | 2.64 | 3.05 | 2.53 | 3.11 | 21.6 | 0.53 |
| CoCr DEB-3Y: 4.5 µg/mm$^2$ | 2.71 | 3.11 | 2.92 | 3.11 | 11.5 | 0.18 |

KEY: CoCr—cobalt chromium stent; PRE—prior to treatment; POST—after treatment; FUP—follow up; LLL—late luminal loss; VD—vessel diameter; MLD—minimum lumen diameter; RD—reference diameter; % DS—percentage diameter stenosis.

According to Table 6, at least the FUP % DS indicates that all doses are effective, 4.5 µg/mm$^2$ (DEB-3Y) being the most effective dose.

15. Four Week Quantitative Coronary Angiography (In Vivo)—Comparison Animal Trial with Drug Eluting Balloons+Stents Two commercial drug balloons, namely, Dior 2$^{nd}$ (Eurocore); and SeQuent (B.Braun) were each provided with a non-drug-eluting stent. The balloons were used in an in vivo Quantitative Coronary Angiography (QCA). The results of the QCA are shown in Table 7 below.

TABLE 7

Results of four week porcine in vivo Quantitative Coronary Angiography (QCA) using commercial drug-eluting balloons.

| Balloon paclitaxel concentration | PRE VD (mm) | POST MLD (mm) | FUP MLD (mm) | FUP RD (mm) | FUP % DS (%) | LLL (mm) |
|---|---|---|---|---|---|---|
| BMS control | 2.49 | 2.98 | 1.12 | 2.72 | 59.3 | 1.85 |
| Dior 2$^{nd}$ + stent (Eurocore) 3 µg/mm$^2$ | 2.41 | 2.94 | 1.43 | 2.73 | 48.4 | 1.41 |
| SeQuent + stent (B. Braun) 3 µg/mm$^2$ | 2.62 | 3.05 | 2.62 | 2.52 | 14.0 | 0.43 |

KEY: BMS—bare metal stent, non-drug-eluting balloon; PRE—prior to treatment; POST—after treatment; FUP—follow up; LLL—late luminal loss; VD—vessel diameter; MLD—minimum lumen diameter; RD—reference diameter; % DS—percentage diameter stenosis.

According to the results of Table 7, the effect of the hydrophobic coating of the present invention provides a late luminal loss effect at least comparable with existing products, with the advantages of controlled and reduced systemic release.

16. Balloon Preparation

A balloon is prepared by coating the outer surface with a carboxymethylcellulose hydrophilic substance, then overcoating the hydrophilic substance with sirolimus and allowing the coating to dry. The sirolimus is disposed exclusively between the balloon folds and a concentration of 1.5 µg/mm$^2$.

17. Retention Property of Hydrophilic Coating in Water (In Vitro)

A balloon is prepared according to experiment 16. In the uninflated state, the balloon is passed three times through a guiding catheter and coronary model in a water bath at 37 deg C. Analysis of the amount of sirolimus remaining on the balloon indicates a reduction of less than 1% of the total load.

18. Retention Property of Hydrophilic Coating in an Ex Vivo Model Living Porcine Artery Three balloons are prepared according to experiment 16, having a concentration of sirolimus of 0.75 µg/mm$^2$, 1.5 µg/mm$^2$ and 4.5 µg/mm$^2$. Each balloon is placed in ex vivo model living porcine artery forming a closed loop model. Concentration of sirolimus dispersed in the system prior to inflation is measured, and the results show that systemic effect of sirolimus in the blood stream is negligible.

19. Retention Property of Hydrophilic Coating (In Vitro)

A balloon is prepared according to experiment 16. The balloon is repeatedly inflated and deflated in both wet and dry conditions, and visually inspected for cracking or other changes to the integrity of the surface. There is no cracking of the coating that could lead to particle release when the surface is analysed at 300× magnification.

20. Effect of Radiation Sterilization

A balloon is prepared according to experiment 16. The balloon is sterilized by irradiation with a gamma-ray source under standard conditions. Analysis by HPLC of the sirolimus on the balloon shows a variation in sirolimus of less than 3% between repeated products tested.

21. Concentration on Balloon Vs Concentration Administered (Ex Vivo)

Three balloons are prepared according to experiment 16, having a concentration of sirolimus of 0.75 μg/mm², 1.5 μg/mm² and 4.5 μg/mm². Each is inserted into an ex vivo model living porcine artery, and inflated for 30 seconds. The dose of sirolimus delivered to the arterial wall is measured. The dose administered is approximately directly proportional to the concentration of sirolimus on the balloon.

22. Multiple Dose Administrations at the Same Location (Ex Vivo)

A balloon is prepared according to experiment 16. It is inserted into an ex vivo model living porcine artery, and inflated for 30 seconds then deflated. This is repeated a further 2 times in the same location. The dose of sirolimus delivered to the arterial wall is measured after each deflation. The dose administered to the wall increases with each inflation i.e. there is a cumulative effect.

What is claimed is:

1. A process for making a folded composition-eluting balloon catheter having a proximal end and a distal end, comprising an elongated catheter tube with an inflation lumen extending therewithin and at least one inflatable balloon having a central longitudinal balloon axis towards the distal end in fluid communication with the inflation lumen, wherein the balloon in an uninflated condition is configured as one or more foldable wings, wherein the balloon in a folded condition comprises a relief structure comprising at least one groove on the outside of the one or more foldable wings, configured to substantially reduce in depth in an inflated condition of the balloon, wherein the at least one groove crosses an outer edge of at least one of the one or more foldable wings, the process comprising the steps of:
   a) coating one or both surfaces of the one or more foldable wings with a hydrophilic coating such that one or both surfaces of the one or more foldable wings are provided with a coated surface;
   b) applying a composition as a coating on the coated surface from step a), such that the composition is provided essentially exclusively within a fold of the one or more foldable wings; and
   c) after step b), folding the one or more foldable wings around the central longitudinal balloon axis, thereby providing a folded composition-eluting balloon,
   wherein the relief structure seals the composition between the fold of the one or more foldable wings to prevent and/or reduce a release of the composition until after an inflation of the balloon of the composition-eluting balloon catheter.

2. The process according to claim 1, wherein the composition is applied in a solution of an organic solvent.

3. The process according to claim 2, wherein the organic solvent comprises ethanol.

4. The process according to claim 2, wherein the organic solvent comprises at least one of methanol, propanol, acetone or ethyl acetate.

5. The process according to claim 1, wherein the composition comprises paclitaxel.

6. The process according to claim 1, wherein the composition comprises at least one of:
   one or more of paclitaxel, melatonin, thalidomide, sirolimus, zotarolimus, everolimus, biolimus, 17-13 estradiol, actinomucin D, docetaxel, and/or any derivatives thereof, or
   one or more of cis-platin, paclitaxel, etoposide, amasecrine, teniposide, irinotecan, toptecan, doxorubicin, epirubicin, bleomycin, and/or any derivatives thereof, or
   one or more of penicillin, erythromycin, ampicillin, clindamycin, tetracycline, streptomycin, amoxicillin, cefaclor, lincomycin, clarithromycin, cephalosporins, azithromycin, doxycycline, ciprofloxacin, cefuroxime, levofloxacin, chloramphenicol, minocycline, penicillins, vancomycin, kanamycin, gentamicins, neomycin, ceftriaxone, bacitracin, oxacillin, cloxacillin, cephalothin, amoxicillin, dicloxacillin, aminoglycosides, methicillin, carbenicillin, gentamicin, trimethoprim, oxytetracycline, rifampin, tetracyclines, polymyxins, cephalexin, chlortetracycline, metronidazole and/or any derivatives thereof.

7. The process according to claim 1, wherein the composition comprises paclitaxel, wherein paclitaxel is applied in a solution comprising ethanol.

8. The process according to claim 1, wherein the composition comprises a polymer, wherein a dilute first coating solution of the polymer is applied as a primer to promote adhesion of a subsequent second coating layer comprising a medicament.

9. The process according to claim 1, further comprising, after step c), the step of removing an excess amount of the composition from the coated surface of the balloon.

10. The process according to claim 1, wherein step b) comprises applying the composition to only a part of the coated surface.

11. The process according to claim 1, wherein the hydrophilic coating is at least one of polyvinylpyrrolidone (PVP) or copolymers containing N-vinylpyrrolidone, poly (meth) acrylic acid or copolymers containing (meth) acrylic acid or (meth) acrylic acid esters, polyacrylamides, polyvinylalcohol and copolymers of partially saponified vinylacetate copolymers, polyethyleneglycol, polyvinylmethylether, polyvinylmethylether-maleic anhydride and copolymers containing maleic-anhydride or maleic-acid esters or copolymers containing vinylmethylether, or copolymers thereof, or water soluble polysaccharides or derivatives thereof or xanthan or a derivative thereof.

12. The process according to claim 1, further comprising providing the folded composition-eluting balloon catheter with a stent.

13. The process according to claim 12, wherein the stent is made from one or more of stainless steel, tantalum, titanium alloy, nitinol, cobalt alloy, cobalt-chromium-nickel alloy, cobalt-chromium alloy, cobalt-chromium F562, or magnesium alloys.

14. The process according to claim 1, wherein the at least one groove has a directional component which is transverse to the central longitudinal axis of the inflatable balloon.

15. The process according to claim 1, whereby the at least one groove extends at a predetermined angle with regard to the longitudinal axis of the inflatable balloon.

16. The process according to claim 1, wherein at least two grooves extend from the distal end to the proximal end of the inflatable balloon and cross each other.

17. The process according to claim 1, wherein the at least one groove is ring or oval shaped, and has a directional component which is transverse to a central longitudinal axis of the inflatable balloon.

18. The process according to claim 1, wherein the relief structure is provided by crimping a pattern by an application of a radial pressure to an outer surface of the folded balloon.

19. The process according to claim 1, further comprising providing the composition-eluting balloon catheter with a guidewire lumen for a rapid exchange catheter or an over the wire catheter mode of operation.

20. A process for making a folded composition-eluting balloon catheter having a proximal end and a distal end, comprising an elongated catheter tube with an inflation lumen extending therewithin and at least one inflatable balloon having a central longitudinal balloon axis towards the distal end in fluid communication with the inflation lumen, wherein the balloon in an uninflated condition is configured as one or more foldable wings, wherein the balloon in a folded condition comprises a relief structure comprising at least one groove on the outside of the one or more foldable wings, configured to substantially reduce in depth in an inflated condition of the balloon, wherein the at least one groove crosses an outer edge of at least one folded wing, the process comprising the steps of:
a) coating one or both surfaces of the one or more foldable wings with a mixture comprising a hydrophilic coating and a composition, such that the composition is provided essentially exclusively within a fold of the one or more foldable wings; and
b) after step a), folding the one or more foldable wings around the central longitudinal balloon axis, thereby providing a folded composition-eluting balloon,
wherein the relief structure seals the composition between the fold of the one or more foldable wings to prevent and/or reduce a release of the composition until after an inflation of the balloon of the composition-eluting balloon catheter.

21. The process according to claim 20, wherein the composition comprises paclitaxel, wherein paclitaxel is applied in a solution comprising ethanol.

22. The process according to claim 20, wherein the composition comprises at least one of:
one or more of paclitaxel, melatonin, thalidomide, sirolimus, zotarolimus, everolimus, biolimus, 17-13 estradiol, actinomucin D, docetaxel, and/or any derivatives thereof, or
one or more of cis-platin, paclitaxel, etoposide, amasecrine, teniposide, irinotecan, toptecan, doxorubicin, epirubicin, bleomycin, and/or any derivatives thereof, or
one or more of penicillin, erythromycin, ampicillin, clindamycin, tetracycline, streptomycin, amoxicillin, cefaclor, lincomycin, clarithromycin, cephalosporins, azithromycin, doxycycline, ciprofloxacin, cefuroxime, levofloxacin, chloramphenicol, minocycline, penicillins, vancomycin, kanamycin, gentamicins, neomycin, ceftriaxone, bacitracin, oxacillin, cloxacillin, cephalothin, amoxicillin, dicloxacillin, aminoglycosides, methicillin, carbenicillin, gentamicin, trimethoprim, oxytetracycline, rifampin, tetracyclines, polymyxins, cephalexin, chlortetracycline, metronidazole and/or any derivatives thereof.

* * * * *

UNITED STATES PATENT AND TRADEMARK OFFICE
CERTIFICATE OF CORRECTION

PATENT NO.         : 9,610,427 B2
APPLICATION NO.    : 15/085745
DATED              : April 4, 2017
INVENTOR(S)        : Ronald Adrianus Maria Horvers It is certified that error appears in the above-identified patent and that said Letters Patent is hereby corrected as shown below:

In the Specification

In Column 3 at Line 34, Change "actinomucin" to --actinomycin--.

In Column 3 at Lines 36-37, Change "amasecrine," to --amsacrine,--.

In Column 3 at Line 37, Change "toptecan," to --topotecan,--.

In Column 3 at Line 59, Change "poly (meth) acrylic acid" to --poly(acrylic acid), poly(methacrylic acid)--.

In Column 4 at Line 1, Change "Xanthane" to --xanthan--.

In Column 8 at Line 60, Change "FIG." to --FIGS.--.

In Column 9 at Line 48, Change "and U.S. Pat. No. 5,120,816," to --, U.S. Pat. No. 5,120,816,--.

In Column 9 at Line 57, Change "poly (meth) acrylic" to --poly(acrylic), poly(methacrylic)--.

In Column 9 at Line 66, Change "Xanthane" to --xanthan--.

In Column 10 at Line 4, Change "polyvinyl pyrrolidone" to --polyvinylpyrrolidone--.

In Column 10 at Line 5, Change "polyvinyl pyrrolidone" to --polyvinylpyrrolidone--.

In Column 15 at Line 1, Change "capronolactone," to --caprolactone,--.

In Column 15 at Line 4, Change "D, L-" to --D,L- --.

Signed and Sealed this
Twenty-ninth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,610,427 B2

In Column 15 at Line 6, Change "polyethylene oxide" to --poly(ethylene oxide)--.

In Column 15 at Lines 8-9, Change "polyD,L-lactide-co-caprolac-tone" to --poly(D,L-lactide-co caprolactone)--.

In Column 15 at Lines 10-11, Change "poly(phoshate" to --poly(phosphate--.

In Column 15 at Line 11, Change "poly(hydroxyl butyrate)" to --polyhydroxybutyrate--.

In Column 15 at Line 32, Change "oesophasgus." to --oesophagus.--.

In Column 15 at Lines 49-50, Change "oesophasgus," to --oesophagus,--.

In Column 15 at Line 50, Change "uretheral duct," to --urethral duct,--.

In Column 15 at Lines 65-66, Change "actinomucin" to --actinomycin--.

In Column 16 at Line 6, Change "amasecrine," to --amsacrine,--.

In Column 16 at Line 6, Change "toptecan," to --topotecan,--.

In Column 18 at Line 54, Change "sarginine," to --arginine,--.

In Column 21 at Lines 64-65, Change "poly(anhydrides)," to --polyanhydrides,--.

In Column 22 at Line 37, Change "Polyoxaesters" to --Polyoxaesters,--.

In Column 22 at Line 49, Change "polyalkyl oxides" to --polyalkyl oxides,--.

In Column 22 at Line 52, Change "polyvinyl pyrrolidinone" to --polyvinylpyrrolidinone--.

In Column 22 at Line 58, Change "polyvinyl chloride" to --poly(vinyl chloride)--.

In Column 22 at Lines 58-59, Change "poly-vinyl methyl ether" to --poly(vinyl methyl ether);--.

In Column 22 at Lines 59-60, Change "polyvinylidene fluoride" to --poly(vinylidene fluoride)--.

In Column 22 at Line 60, Change "polyvinylidene chloride" to --poly(vinylidene chloride)--.

In Column 22 at Line 62, Change "polyvinyl acetate" to --poly(vinyl acetate)--.

In Column 23 at Line 5, Change "hydoxyalkyl" to --hydroxyalkyl--.

In Column 24 at Line 64, Change "U.S. Pat. No. 6,585,764," to --U.S. Pat. No. 6,585,764 and--.

CERTIFICATE OF CORRECTION (continued)
U.S. Pat. No. 9,610,427 B2

In the Claims

In Column 34 at Line 3, In Claim 6, change "actinomucin" to --actinomycin--.

In Column 34 at Lines 5-6, In Claim 6, change "amasecrine," to --amsacrine,--.

In Column 34 at Line 6, In Claim 6, change "toptecan," to --topotecan,--.

In Column 34 at Line 58, In Claim 15, change "whereby" to --wherein--.

In Column 36 at Line 12, In Claim 22, change "actinomucin" to --actinomycin--.

In Column 36 at Lines 14-15, In Claim 22, change "amasecrine," to --amsacrine,--.

In Column 36 at Line 15, In Claim 22, change "toptecan," to --topotecan,--.